(12) United States Patent
Honjo et al.

(10) Patent No.: US 7,858,746 B2
(45) Date of Patent: Dec. 28, 2010

(54) SUBSTANCE THAT SPECIFICALLY RECOGNIZES PD-1

(75) Inventors: Tasuku Honjo, 19-4, Ohsagi-cho, Iwakura, Sakyo-ku, Kyoto-shi, Kyoto (JP) 606-0001; Shiro Shibayama, Mishima-gun (JP); Masayoshi Matsuo, Mishima-gun (JP); Takao Yoshida, Mishima-gun (JP)

(73) Assignees: ONO Pharmaceutical Co., Ltd., Osaka (JP); Tasuku Honjo, Kyoto (JP)

( * ) Notice: Subject to any disclaimer, the term of this patent is extended or adjusted under 35 U.S.C. 154(b) by 392 days.

(21) Appl. No.: 12/057,637

(22) Filed: Mar. 28, 2008

(65) Prior Publication Data

US 2009/0076250 A1 Mar. 19, 2009

Related U.S. Application Data

(62) Division of application No. 10/485,466, filed as application No. PCT/JP02/07735 on Jul. 30, 2002, now abandoned.

(30) Foreign Application Priority Data

Jul. 31, 2001 (JP) .......................... P.2001-232303

(51) Int. Cl.
*C07K 14/00* (2006.01)
(52) U.S. Cl. ..................................................... 530/350
(58) Field of Classification Search ...................... None
See application file for complete search history.

(56) References Cited

U.S. PATENT DOCUMENTS 5,629,204 A 5/1997 Honjo et al.
7,029,674 B2 4/2006 Carreno et al.

FOREIGN PATENT DOCUMENTS

WO WO 01/14557 A1 3/2001
WO WO 02/078731 A1 10/2002

OTHER PUBLICATIONS

Okazaki T., et al., PD-1 immunoreceptor inhibits B cell receptor-mediated signaling by recruiting src homology 2-domain-containing tyrosine phosphatase 2 to phosphotyrosine, Proc. Natl. Acad. Sci., USA, 2001, 98(24):13866-13871.
Freeman, G.J., et al., Engagement of the PD-1 immunoinhibitory receptor by a novel B7 family member leads to negative regulation of lymphocyte activation, J. Exp. Med., 2000, 192(7): 1027-1034.
Nishimura, et al., Immunological studies on PD-1 deficient mice: implication of PD-1 as a negative regulator for B cell responses, Int. Immunol., 1998, 10(10):1562-1572.
XP-001064842—(2001) Yvette Latchman et al., "PD-L2 is a second ligand for PD-1 and inhibits T cell activation", Nature Immunology, Nature Publishing Group, vol. 2, No. 3, pp. 261-268.
XP-002189416—(2001) Su-Yi Tseng et al., "B7-DC, a New Dendritic Cell Molecule with Potent Costimulatory Properties for T Cells", J. Exp. Med., vol. 193, No. 7, pp. 839-845.
XP-000971788—(1999) Hiroyuki Nishimura et al., "Development of Lupus-like Autoimmune Diseases by Disruption of the PD-1 Gene Encoding an ITIM Motif-Carrying Immunoreceptor", Cell Press, vol. 11, No. 2, pp. 141-151.
XP-002973917—(2002) Julia Brown et al., "Blockade of PD-1 ligands on dendritic cells enhances T cell activation and cytokine production", Federation of American Societies for Experimental Biology, vol. 16, No. 4, A710, 5174.
Partial European Search Report dated Dec. 5, 2005.
Abbas, et al., Cellular and Molecular Immunology, 2003, Elsevvier Science, pp. 114-171.
Webster's New World Dictionary, 1988, Simon & Schuster, pp. 1121 and 1335.
Blazar, et al., J. Immunol., 1996, 157:3250-3259.
Bach J., Immunology Today, 1993, 14:322-326.

*Primary Examiner*—Ilia Ouspenski
(74) *Attorney, Agent, or Firm*—Sughrue Mion, PLLC

(57) ABSTRACT

Compounds that can recognize selectively both PD-1 protein and a membrane protein co-existing with PD-1 on a cell membrane, and can transmit a suppressive signal of PD-1. The compounds are useful for medical treatment and/or prevention of diseases caused by immune abnormality.

2 Claims, 3 Drawing Sheets

SUBSTANCE THAT SPECIFICALLY RECOGNIZES PD-1

This is a divisional of application Ser. No. 10/485,466 filed Feb. 2, 2004, now abandoned which is the National Stage of PCT/JP02/07735 filed Jul. 30, 2002, and which claims priority from Japanese Application No. 2001-232303 filed Jul. 31, 2001. The entire disclosures of the prior applications are hereby incorporated by reference.

TECHNICAL FIELD

The invention is related to a substance comprising a substance that recognizes PD-1, a substance that recognizes a membrane protein co-existing with PD-1 on a cell membrane, and a linker.

BACKGROUND

The immune system acquired the mechanism that can respond to various foreign antigens. The mechanism brings about the diversity of an antigen receptor by recombination of V, (D) and J fragment in T cells and B cells. Although this mechanism brought a result that produces self-reactive lymphocytes simultaneously, these self-reactive lymphocytes are removed by the negative selection in the thymus or bone marrow, and are further controlled by the self-tolerance mechanism of clone removal or anergy in the periphery.

Although it is thought that an autoimmune disease is developed by the breakdown of self-tolerance, the researches using various disease model mice have been made towards the elucidation of the mechanism of pathogenesis of the disease. However, there are many still unknown matters about the etiology of an autoimmune disease and the molecular mechanism of self-tolerance. In such a situation, existence of the mouse which shows the symptoms of an autoimmune disease with a single gene deficit is very important, when trying to study the etiology of an autoimmune disease from a molecular biological viewpoint. CTLA4-/-mouse which causes lethal systemic lymphocytes infiltration (Waterhouse P. et. al., Science 270:985~988, 1995, Tivol E. A. et. al., Immunity 3:541~547, 1995), SHP-1 deficit mothaten mice (Shulltz L. D. et. al., Cell 73: 1445~1454, 1993), TGF-beta-1 knockout mouse (Shull M. M. et. al., Nature 359:693-699, 1992), lyn-/-mouse which shows the symptoms of glomerular nephritis (Hibbs M. L. et. al., Cell 83:301-311, 1995), and FCRIIB-/-mouse (Bolland S. & Ravetch J. V., Immunity 13:277-285, 2000) are the representation, and the relation of these molecules and self-tolerance is studied.

PD-1 is type I membrane protein of 55 kD belonging to an immunoglobulin family. Bothmouse PD-1 and human PD-1 consist of 288 amino acids, and have signal peptide at N terminal (20 amino acid) and hydrophobic region in the middle part, which is a transmembrane region (The EMBO J. 11 (11):3887-3895, 1992); Japanese patent Publication No. 5-336973; EMBL/GenBank/DDJB Acc. No. X67914, Genomics 23:704, 1994; Japanese patent Publication No. 7-291996 (U.S. Pat. No. 5,629,204).

In a thymocyte, PD-1 is expressed during a CD4-CD8- cell differentiation to a CD4+CD8+ cell (Nishimura H. et. al., Int. Immunol. 8:773-780, 1996, Nishimura H. et. al., J. Exp. Med. 191:891-898, 2000). Moreover, in the periphery, PD-1 is expressed in T cells and B cells which were activated by the stimulus from an antigen receptor (AgataY. et. al., Int. Immunol. 8:765-772, 1996), and in bone marrow cells including activated macrophage.

PD-1 has ITIM (Immunoreceptor tyrosine-based inhibitory motif) in its intracellular region, therefore it is considered to be a negative regulator in immune reaction. PD-1 deficit mice develop a lupus-like autoimmune disease such as glomerular nephritis and arthritis (C57BL/6 genetic background) (Nishimura H. et. al., Int. Imuunol. 10:1563-1572, 1998, Nishimura H. et. al., Immunity 11:141-151, 1999) and dilated cardiomyopathy-like disease (BALB/c genetic background) (Nishimura H. et. al., Science 291:319-322, 2001), it became clear that PD-1 is a regulator of the development of autoimmune disease, especially one of self-tolerance in the periphery.

DISCLOSURE OF THE INVENTION

It is thought that PD-1 is the regulator of various autoimmune diseases, and that it is one of the genes that cause an autoimmune disease. By controlling the function of PD-1, it thought that the medical treatment and diagnosis of suppression or enhancement of the immune function, infection, the rejection at the time of a transplant, a neoplasm, etc. could be performed, and as a result of repeating examination wholeheartedly, the inventors reached this invention concerning the substance which controls the function of PD-1.

The stimulus to lymphocytes which control immunity is transmitted mainly through T cell receptor (TCR) in the case of T cells, and B cell receptor (BCR) in the case of B cells, and the intracellular phosphorylation play an important role in its molecular mechanism.

Since it became clear that PD-1 is controlling negatively various cells responsible for immunity, such as lymphocytes and myeloid cells etc., and PD-1 has ITIM (Immunoreceptor tyrosine-based inhibitory motif) in its intracellular region, the inventors considered the molecular mechanism involved in the inhibitory signal transduction of PD-1 to be the recruit of de-phosphorylation enzymes (phosphatases). Therefore, it came to be considered by locating PD-1 near TCR or BCR that it can display the function of PD-1. The inventors confirmed that the inhibitory signal of PD-1 was transmitted with the substance in which PD-1 was cross-linked to TCR or BCR, and completed this invention.

The inventors confirmed first that the above-mentioned idea was right using anti-PD-1 antibody, and anti-BCR antibody or anti-CD3 antibody. CD3 is the membrane protein expressed on a T cell, and is one component of the complexes that constitute TCR. The divalent antibody was constructed by bridging anti-PD-1 antibody and anti-BCR or anti-CD3 antibody. In the present invention, this divalent antibody is called hybrid antibody. The inventors produced this hybrid antibody for the first time.

Moreover, the knowledge that a signal transmits by cross-linking two kind of receptors using this hybrid antibody is also acquired for the first time.

Namely, the present invention relates to,

1. A substance comprising a substance that recognizes PD-1, a substance that recognizes a membrane protein co-existing with PD-1 on a cell membrane, and a linker,
2. The substance according to (1), which is a divalent substance comprising a substance that recognizes PD-1, a substance that recognizes a membrane protein co-existing with PD-1 on a cell membrane, and a linker,
3. The substance according to (1) or (2), in which a membrane protein is a protein existing on a T cell membrane or B cell membrane,
4. The substance according to (1) or (2), which comprises a substance that recognizes PD-1, a substance that recognizes a protein constituting T cell receptor complex or a substance that recognizes a protein constituting B cell receptor complex, and a linker, 5. The substance according to any one of (1) to (4), in which a substance that recognizes PD-1 and in which a substance that recognizes a protein is dimer to pentamer, respectively, 6. The substance according to any one of (1) to (5), in which one of or both substance that recognizes PD-1 and substance that recognizes a protein are an antibody, 7. The substance according to any one of (1) to (6), in which one of the two or both substance that recognizes PD-1 and substance that recognizes a protein are a Fab portion of antibody, 8. The substance according to any one of (1) to (5), in which a linker comprises an organic compound, 9. The substance according to any one of (1) to (5), in which a linker comprises a peptide, 10. The substance according to any one of (1) to (5), in which a substance that recognizes PD-1 and in which a substance that recognizes a protein is a peptide, respectively, 11. The substance according to any one of (1) to (5), in which a substance that recognizes PD-1 and in which a substance that recognizes a protein comprises two or more peptides including a heavy chain variable region and a light chain variable region of antibody, respectively, 12. The substance according to any one of (1) to (5), in which a substance that recognizes PD-1, in which a substance that recognizes a protein, and in which a linker is a peptide, respectively, 13. A pharmaceutical composition containing an effective dose of the substance according to (1) for the medical treatment and/or prevention of a disease in which PD-1 participates, 14. The pharmaceutical composition according to (13), in which disease is selected from the group consisting of neurodegenerative disease, autoimmune disease, organ transplant rejection, neoplasm and infection, 15. The pharmaceutical composition according to (14), in which neurodegenerative disease is selected from the group consisting of Parkinson's disease, parkinsonian syndrome, Huntington's disease, Machado-Joseph disease, amyotrophic lateral sclerosis and Creutzfeldt-Jakob disease, 16. The pharmaceutical composition according to (14), in which autoimmune disease is selected from the group consisting of glomerular nephritis, arthritis, dilated cardiomyopathy-like disease, ulcerative colitis, Sjogren's syndrome, Crohn's disease, systemic lupus erythematosus, chronic rheumatoid arthritis, multiple sclerosis, Psoriasis, allergic contact dermatitis, polymyositis, scleroderma, periarteritis nodosa, rheumatic fever, vitiligo vulgaris, insulin-dependent diabetes mellitus, Behcet's Syndrome and chronic thyroiditis.

A substance that recognizes PD-1 said by the present invention may be a substance which recognizes PD-1 specifically, for example, anti-PD-1 antibody, the fragment of anti-PD-1 antibody, PD-1 in itself, the fragment of PD-1, ligand of PD-1 (PD-L1 (Freeman G. J. et. al., J. Exp. Med. 192:1027-1034, 2000), PD-L2, PD-H3), the fragment thereof and a low molecule organic compound, etc.

In more concretely, it is anti-PD-1 antibody produced by the hybridoma strain "J43", which was deposited on May 30, 2001 in International Patent Organism Depositary, National Institute of Advanced Industrial Science and Technology, AIST Tsukuba Central 6, 1-1, Higashi 1-Chome Tsukuba-shi, Ibaraki-ken 305-8566 Japan as Accession number FERM P-18356, and transferred to international deposition on Jul. 16, 2002 as international deposition Accession number FERM BP-8118.

Preferably, although it is the Fab portion of the antibody, it is not limited to this.

A substance that recognizes a membrane protein co-existing with PD-1 on a cell membrane said by the present invention may be a substance which recognizes a membrane protein specifically, for example, a substance which specifically recognizes a complex that constitute T cell receptor (TCR) (TCR complex) etc. expressed on T cells, or a substance which specifically recognizes a complex that constitute B cell receptor (BCR) (BCR complex) etc. expressed on B cells, such as the fragment of a protein constituting TCR complex, anti-TCR antibody, the fragment of anti-TCR antibody, the fragment of a protein constituting BCR complex, anti-BCR antibody and the fragment of anti-BCR antibody.

Preferably, although it is the Fab portion of an anti-TCR antibody or the Fab portion of an anti-BCR antibody, it is not limited to these.

Both an anti-TCR antibody and an anti-BCR antibody are available commercially. For example, anti-CD3 antibody (α-CD3ε mAb, manufactured by Pharmingen) as an anti-TCR antibody, and anti-IgG (H+L) polyclonal antibody (manufactured by Zymed) as an anti-BCR antibody are available, respectively.

A linker said by the present invention may be a substance which can connect the above mentioned substance recognizing PD-1 and the substance recognizing a membrane protein co-existing with PD-1 on a cell membrane if a suitable distance can be maintained. More specifically, it may be a peptide, amide, etc.

A linker can be used what is marketed, for example, Phenylenedimaleimide (manufactured by Aldrich) is available.

A substance that specifically recognizes PD-1, which is the subject of the present invention, can be produced as follows, for example.

In the case that an antibody is chosen as a substance which recognizes PD-1 specifically, and that an antibody is also chosen as a substance which recognizes specifically a membrane protein co-existing with PD-1 on a cell membrane (hereinafter, simply referred to as "the membrane protein")), a substance is called hybrid antibody by this invention. The method of producing this hybrid antibody is explained.

(1) Animals are immunized with PD-1 or the membrane protein as an antigen, (2) Spleen cells from the immunized animal and myeloma cells are fused, (3) Cells producing monoclonal antibody against the antigen (PD-1 or the membrane protein) are screened among thus obtained hybridoma cells, (4) Aimed hybridoma cells are cloned, (5) Cloned hybridoma cells are grown, (6) Antibodies produced are isolated and purified, (7) A hybrid antibody can be produced by bridging thus obtained anti-PD-1 antibody and anti-membrane antibody with a linker.

Alternatively, (8) To obtain F(ab')$_2$, the antibodies produced are treated with pepsin, isolated and purified, (9) Each F(ab')$_2$ thus prepared is reduced, isolated and purified,

(10) A hybrid antibody can be produced by bridging each F(ab')$_{SH}$ thus prepared with a linker.

In the case that both or one of the two of a substance which specifically recognizes PD-1 and a substance which specifically recognizes a membrane protein co-existing with PD-1 on a cell membrane (the membrane protein) are a low molecule organic compound,

(11) A low molecule compound which inhibits the binding of each antibody to PD-1 or the membrane protein which is a corresponding antigen, respectively, is found out by using antibody produced by the above-mentioned technique and suitable detection equipment,

(12) A substance can be produced by bridging the compound-to-compound, the compound to antibody, or the compound to Fab with a linker.

It is as follows when each step is explained more concretely.

In an immunization step (1), it is desirable to administer PD-1 or the membrane protein to an animal into the peritoneal cavity or footpad. Moreover, the animal to be immunized will not be limited especially if it is the one from which the monoclonal antibody is obtained generally such as mouse, rat or the like. In the case of a mouse, the amount of an antigen is enough if 10-200 micrograms is administered per time.

The cell fusion of (2) is carried out by excising spleen from an immunized animal with which the antibody titer has fully risen among the animals immunized in the step (1), preparing spleen cell suspension according to a usual method, and adding polyethylene glycol (preferably PEG4000) to a mixture of the spleen cells thus obtained and myeloma cells at 37° C. Some kinds, such as P3X63Ag8, P3/NS1/1-Ag4-1, and SP-2/0-Ag-14, are known as the mouse myeloma cell, and all of them are easily available.

As the myeloma cell, HGPRT (hypoxanthine-guanine phosphoribosyl transferase)-defective cell line which cannot survive in HAT medium (a medium containing hypoxanthine, aminopterin and thymidine) is useful, and it is further preferred that it is a cell line in which the myeloma cells themselves do not secrete any antibody. Preferably, SP-2/O—Ag-14 is used.

Next, the obtained cell fusion mixture is dispensed into a 96-well micro plate at a low density, and cultivated in the HAT medium. By culturing them for 1 to 2 weeks, un-fused myeloma cells, hybridomas of myeloma cells themselves, un-fused spleen cells and dybridomas of spleen cells themselves die because their surviving conditions are not satisfied, and only the hybridomas of spleen cell with myeloma cell are propagated.

In the screening of (3), whether or not a hybridoma is the one which produces an antibody against PD-1 or the membrane protein is judged by allowing each hybridoma culture supernatant to react with the immobilized antigen, and then determining amount of the antibody in the supernatant specifically adsorbed to the antigen using a labeled second antibody.

The step (4) is carried out by cloning the antibody-producing hybridoma in accordance with the soft agar culture method (Monoclonal Antibodies, 372 (1980)). In this case, it is also possible to use the limiting dilution method.

The step (5) is carried out by culturing the cloned hybridoma in usual medium and then separating and purifying from the culture supernatant, however, to obtain a larger amount of the antibody efficiently a method in which the hybridoma is administered into the abdominal cavity of mouse, allowed to propagate therein and then separated and purified from the ascites is used.

In the step (6), the purification can be carried out by usual methods such as salting out, ion exchange chromatography, gel filtration, hydrophobic chromatography and affinity chromatography, however, affinity chromatography using protein A-sepharose CL-4B (manufactured by Amersham Bioscience) is used more effectively.

Since a hybrid antibody of the present invention recognizes PD-1 specifically, it can be used for the purification and concentration of PD-1, for example, for affinity chromatography etc.

The step (7) can be carried out by bridging a linker such as sulfo-EMCS (N-(6-maleimidcaproxy) sulfo-succinimide sodium salt) to amide groups or SH (mercapto) groups of an antibody. First, one antibody is combined to sulfo-EMCS by amide coupling, un-reacted sulfo-EMCS is discarded by gel filtration, the maleimide groups of the sulfo-EMCS that is bound to the first antibody is reacted with SH (mercapto) groups of the other antibody that is reduced with 2-mercaptoethylamine etc., and then a substance bridged over two kinds of antibodies is size-fractionated using gel filtration.

The step (8) is carried out by digesting each antibody obtained in the step (6) with pepsin at 37° C. for 48 hours. The separation and purification of F(ab')$_2$ digested with pepsin can be carried out by usual methods such as salting out, ion exchange chromatography, gel filtration, hydrophobic chromatography and affinity chromatography, however, gel filtration using Sephacryl S-200 (manufactured by Amersham Bioscience) is used more effectively.

The step (9) is carried out by reducing F(ab')$_2$ with 2-mercaptoethanol at 30° C. for 30 minutes. The separation and purification of the reduced Fab$_{SH}$ can be carried out by usual methods such as salting out, ion exchange chromatography, gel filtration, hydrophobic chromatography and affinity chromatography, however, gel filtration using Sephacryl S-200 is used more effectively.

In the step (10), Fab$_{SH}$ fraction of one antibody is combined with a linker. As a linker, a substance that is combinable with mercapto (SH) groups of Fab$_{SH}$ may be used, for example, a reaction is performed by adding phenylene dimaleimide for 30 minutes at room temperature. Next, the reaction is followed by adding the other Fab$_{SH}$ multiplied by 1.3 at room temperature for 4 hours. The separation and purification of bispecific substance can be carried out by usual methods such as salting out, ion exchange chromatography, gel filtration, hydrophobic chromatography and affinity chromatography, however, gel filtration using Sephacryl S-200 is used more effectively.

The step (11) can be carried out by using the antibody obtained at the step (6) without modification, or by using the antibody with appropriate labeling (for example, biotin-conjugated or FITC-conjugated etc.) in accordance with a usual method. In the case that ELISA method is used, an antigen is immobilized by a usual method, and then an antibody is added. Next, when enzyme-conjugated second antibody and biotin-conjugated antibody are used, enzyme-conjugated streptavidin is added, then the specific binding between antigen and antibody is measured in the presence of chromophore-producing substance by using absorptiometer. By using this assay system a low molecule that specifically recognizes PD-1 or the membrane protein can be obtained.

In the step (12), when one of the two is an antibody or Fab, the obtained low molecule can be combined with the antibody or Fab by introducing the suitable functional group in it. For example, when maleimide groups is introduced, it is possible to make it combine with mercapto groups of an antibody or Fab. Moreover, when both substances are low molecules, it is possible to synthesize a molecule containing both ones.

In the case that an antibody is chosen as a substance which recognizes PD-1 specifically, that an antibody is also chosen as a substance which recognizes specifically a membrane protein co-existing with PD-1 on a cell membrane, and that both antibodies are included in the same peptide, the substance is called bispecific antibody in the present invention. The method of producing this bispecific antibody is explained.

(1) An antibody gene is isolated from hybridoma cells producing antibodies against PD-1 and the membrane protein, respectively, (2) A variable domain of an antibody gene against PD-1 and a variable domain of an antibody gene against the membrane protein are connected using a linker DNA, the connected DNA fragment is inserted to an expression vector, and cells are transfected with the expression vector and propagated, (3) Bispecific antibody can be prepared by separating and purifying the protein thus produced.

It is as follows when each step is explained more concretely.

The step (1) consists of the processes, which isolates RNA from hybridoma cells, and which isolates cDNA encoding an antibody or its partial peptide.

The process which isolates total RNA or mRNA from hybridoma cells can be carried out in accordance with known methods (hereinafter, if unstated especially, a known method is the method described in Molecular Cloning (Sambrook J., Fritsch E. F. and Maniatis T., Cold Spring Harbor Laboratory Press, 1989) or Current Protocol in Molecular Biology (Ausubel F. M. et al., John Wiley & Sons and Inc.).

The cloning of a cDNA encoding an antibody gene or its partial peptide of the present invention can be performed by an amplification using Polymerase Chain Reaction (hereinafter simply referred to as "PCR method") with synthesized DNA primers having partial nucleotide sequence encoding an antibody of the present invention, or by a selection using hybridization of cDNAs inserted into a suitable vector with a labeled DNA fragment or synthetic DNA encoding an antibody of the present invention partially or entirely. Hybridization can be carried out in accordance with known methods. An antibody gene may be amplified directly by using Reverse Transcriptase Polymerase Chain Reaction (hereinafter simply referred to as "RT-PCR method") from total RNA or mRNA.

(2) Bispecific antibody of the present invention may be prepared by:

i) A method of peptide synthesis, or ii) A method of production using recombinant DNA technology, preferably, by the method described in ii) in an industrial production.

Examples of expression system (host-vector system) for the production of peptide by using recombinant DNA technology are the expression systems using bacteria, yeast, insect cells and mammalian cells.

For example, in an *E. Coli* expression system, the initiation codon (ATG) is added to 5'-end of the nucleotide sequence, for example, shown in SEQ ID NO:28, then the expression vector is prepared by connecting the obtained DNA to the downstream of a suitable promoter (e.g., trp promoter, lacpromoter, λ PL promoter, and T7 promoter), and by inserting it into a vector (e.g., pBR322, pUC18 and pUC19) which functions in an *E. coli* strain.

Then, an *E. coli* strain (e.g., *E. coli* strain DH1, *E. coli* strain JM109 and *E. coli* strain HB101) which is transformed with the expression vector described above may be cultured in an appropriate medium to obtain the desired peptide. When a signal peptide of bacteria (e.g., signal peptide of pel B) is utilized, the desired peptide may be released in periplasm. Furthermore, a fusion protein with other peptide may be produced easily.

In a mammalian cell expression system, an expression vector is prepared by inserting a DNA, for example, having the nucleotide sequence shown in SEQ ID NO: 28, into the downstream of a proper promoter (e.g., SV40 promoter, LTR promoter and metallothionein promoter) in a proper vector (e.g., retro virus vector, papilloma virus vector, vaccinia virus vector and SV40 vector). Next, suitable mammalian cells (e.g., monkey COS-1 cells, COS-7 cells, Chinese hamster CHO cells, mouse L cells, 293 cells etc.) are transfected with the expression vector thus obtained, and then the transfected cells are cultured in an appropriate medium, the aimed peptide can be secreted into the culture medium.

A transformation of *E. coli* can be carried out in accordance with the method, for example, described in Proc. Natl. Acad. Sci. (USA) 69:2110, 1972 and Gene 17: 107, 1982.

A transfection of mammalian cells can be carried out in accordance with the method, for example, described in Saiboukougaku supl. 8:263 (New experimental protocol for cell technology), Shujun-sha, 1995 and Virology 52:456, 1973.

It is known that a bispecific antibody can be prepared directly by using recombinant DNA technology. For example, Alt et al. (FEBS Letter 454:90, 1999) reported the generation of a bispecific antibody (it is referred to a single-chain diabody) directed against carcinoembryonic antigen and *E. coli* beta-galactosidase. In said fragment, a heavy chain variable domain (VH) of one antibody is connected to a light chain variable domain (VL) of the other antibody with a short linker, which prevent the pairing of these two continuous domains on the same chain. Therefore, the VH and VL domains of this fragment are obliged to pair with each complementary VL and VH domain on other chain, and thereby form two antigen binding sites.

It is preferred that a peptide linker contains 3 to 12 amino acid residues, but it is not limited particularly to its amino acid sequence (Hudson et al., J. Immunol. Met. 231:177, 1999).

(3) The peptide thus obtained can be purified by usual methods such as salting out, ion exchange chromatography, gel filtration, hydrophobic chromatography and affinity chromatography.

Since bispecific antibody of the present invention also recognizes PD-1 specifically, it can be used for the purification and concentration of PD-1, for example, for affinity chromatography etc.

INDUSTRIAL APPLICABILITY

Application for Pharmaceuticals

The greatest and important usage of a substance that specifically recognizes PD-1 by the present invention is for the medical treatment of the following disease.

A substance that specifically recognizes PD-1 by the present invention is useful for the medical treatment and/or prevention of diseases such as neurodegenerative disease (Parkinson's disease, parkinsonian syndrome, Huntington's disease, Machado-Joseph disease, amyotrophic lateral sclerosis and Creutzfeldt-Jakob disease etc.).

A substance that specifically recognizes PD-1 by the present invention is also useful for the medical treatment and/or prevention of diseases, in which PD-1 is involved and immune responses are enhanced, such as autoimmune diseases (glomerular nephritis, arthritis, dilated cardiomyopathy-like disease, ulcerative colitis, Sjogren's syndrome, Crohn's disease, systemic lupus erythematosus, chronic rheumatoid arthritis, multiple sclerosis, Psoriasis, allergic contact dermatitis, polymyositis, scleroderma, periarteritis nodosa, rheumatic fever, vitiligo vulgaris, insulin-dependent diabetes mellitus, Behcet's Syndrome and chronic thyroiditis etc.), organ transplant rejection, and allergy.

A substance that specifically recognizes PD-1 by the present invention is also useful for the medical treatment and/or prevention of diseases, in which PD-1 is involved and immune responses are reduced, such as neoplasm and infections.

For the above mentioned usage, administration of the substance that specifically recognizes PD-1 by the present invention can be carried out in systemic or local, generally peroral or parenteral ways.

The dosage to be administered depends upon age, body weight, symptom, desired therapeutic effect, route of administration, and duration of the treatment etc. In human adults, one dose per person is generally between 0.1 mg and 100 mg by oral administration up to several times per day, or between 0.01 mg and 30 mg by parenteral administration (preferably intravenous administration) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as inner solid compositions or inner liquid compositions for oral administration, or as injections, liniments or suppositories etc. for parenteral administration.

Examples of Inner solid compositions for oral administration include compressed tablets, pills, capsules, dispersible powders and granules etc. Examples of capsules include hard capsules and soft capsules.

In such inner solid compositions, one or more of the active compound(s) remains intact, or is/are admixed with excipients (lactose, mannitol, glucose, microcrystalline cellulose and starch etc.), connecting agents (hydroxypropyl cellulose, polyvinylpyrrolidone, magnesium metasilicate aluminate, etc.), disintegrating agents (cellulose calcium glycolate etc.), lubricating agents (magnesium stearate etc.), stabilizing agents, assisting agents for dissolving (glutamic acid, asparaginic acid etc.) etc. to prepare pharmaceuticals by known methods. The pharmaceuticals may, if desired, be coated with a coating agent (sugar, gelatin, hydroxypropyl cellulose or hydroxypropylmethyl cellulose phthalate etc.), or be coated with two or more films. Further, coating may include capsules of absorbable materials such as gelatin.

Inner liquid compositions for oral administration may contain pharmaceutically acceptable water-agents, suspensions, emulsions, syrups and elixirs etc. In such liquid compositions, one or more of the active compound(s) is/are resolved, suspended or emulsified in inert diluent (s) commonly used in the art (purified water, ethanol or mixture thereof etc.). Such liquid compositions may also comprise wetting agents, suspending agents, emulsifying agent, sweetening agents, flavoring agents, perfuming agents, preserving agents and buffer agents etc.

Injections for parenteral administration include solutions, suspensions and emulsions and solid injections, which are dissolved or suspended in solvent when it is used. In such compositions, one or more active compound(s) is/are dissolved, suspended or emulsified in a solvent. Solvents include distilled water for injection, physiological salt solution, plant oil, propylene glycol, polyethylene glycol, alcohol such as ethanol, and mixture thereof etc. Such compositions may comprise additional stabilizing agents, assisting agents for dissolving (glutamic acid, asparaginic acid, POLYSOLBATE80 (registered trademark) etc.), suspending agents, emulsifying agents, soothing agent, buffer agents, preserving agents etc. They may be manufactured or prepared by sterilization or by aseptic manipulation in a final process. They may also be manufactured in the form of sterile solid compositions such as freeze-dried compositions, and can be dissolved in sterile water or some other sterile solvent for injection immediately before use.

Other compositions for parenteral administration include liquids for external use, ointments, endermic liniments, aerosols, spray compositions, suppositories and pessaries for vaginal administration etc., which comprise one or more of the active compound(s) and may be prepared by known methods.

Spray compositions may comprise additional substances other than inert diluents generally used: e.g. stabilizing agents such as sodium hydrogen sulfate, buffer agents to give isotonicity, isotonic buffer such as sodium chloride, sodium citrate and citric acid. For preparation of such spray compositions, for example, the methods described in the U.S. Pat. No. 2,868,691 and U.S. Pat. No. 3,095,355 may be used.

Since PD-1 is involved in immune responses, the substance that specifically recognizes PD-1 by the present invention can also be used for the screening of substances, which are involved in immune responses, by measuring the expression of PD-1.

EFFECT OF THE INVENTION

A substance that specifically recognizes PD-1 by the present invention comprises a substance that recognizes PD-1, a substance that recognizes a membrane protein co-existing with PD-1 on a cell membrane, and a linker, is a superior substance recognizable both PD-1 and the membrane protein specifically and transmittable the signal of PD-1.

BEST MODE FOR CARRYING OUT THE INVENTION

Figure 1:
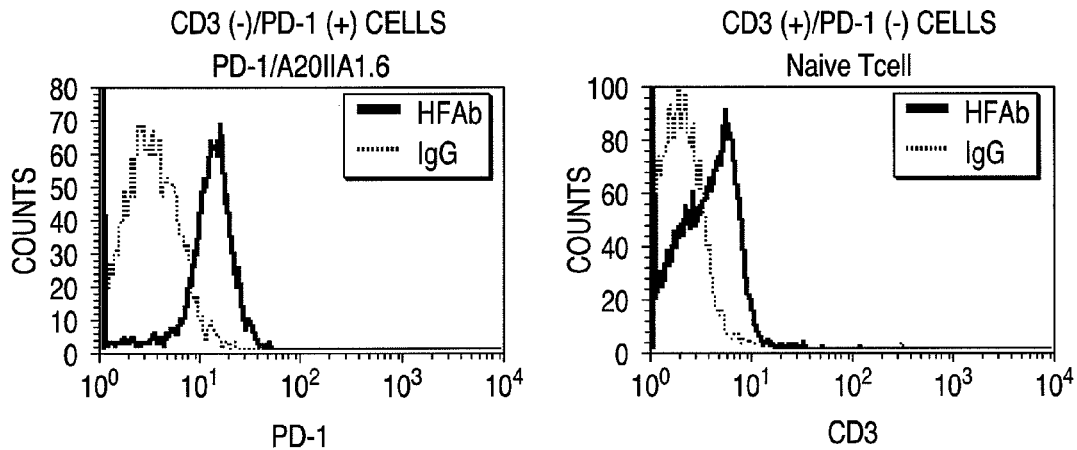
FIG. 1 shows the results of FACS analysis using anti-PD-1/anti-TCR hybrid Fab antibodies.

The present invention is more specifically explained by means of the following examples, but is not limited only to these examples.

Hereinafter, a substance in which anti-PD-1 antibody and anti-T cell receptor antibody are linked by a linker simply referred to as "anti-PD-1/anti-TCR hybrid antibody", and a substance in which anti-PD-1 antibody and anti-B cell receptor antibody are linked by a linker "anti-PD-1/anti-BCR hybrid antibody", respectively. A substance in which the $Fab_{SH}$ portion of anti-PD-1 antibody and the $Fab_{SH}$ portion of anti-T cell receptor antibody are linked by a linker hereinafter simply referred to as "anti-PD-1/anti-TCR hybrid Fab antibody", and a substance in which the $Fab_{SH}$ portion of anti-PD-1 antibody and the $Fab_{SH}$ portion of anti-B cell receptor antibody are linked by a linker "anti-PD-1/anti-BCR hybrid Fab antibody", respectively.

EXAMPLE 1

(1) Preparation of Anti-PD-1/Anti-TCR Hybrid Antibodies (1-A) Introduction of Maleimide to Anti-Mouse CD3ε Monoclonal Antibodies Anti-mouse CD3ε monoclonal antibodies were substituted with Sodium phosphate (0.1M, pH7.0) and Nacl (50 mM), then 200 times quantity of sulfo-EMCS (manufactured by Dojin Chemical) were added and incubated at 20° C. for 1 hour. Then the reaction mixture was size-fractionated by gel filtration using Sephacril S-300 [Sodium phosphate (0.1M, pH7.0)] and major peak fractions were collected by monitoring the absorbency at 280 nm. The protein content was calculated from the absorbency at 280 nm simultaneously.

(1-B) Reduction of Anti-PD-1 Antibodies

Antibodies against mouse PD-1 (produced by the hybridoma cells named (J43) and deposited as international deposition Accession number FERM BP-8118) were substituted with Sodium phosphate (0.1M, pH6.0), added with 2-mercaptoethylamine (final concentration of 10 mM) and EDTA (final concentration of 1 mM), and reduced at 37° C. for 90 minutes. Then the reaction mixture was size-fractionated by gel filtration using Sephacryl S-300 [Sodium phosphate (0.1M, pH6.0)] and major peak fractions (single chain fractions) were collected by monitoring the absorbency at 280 nm. The protein content was calculated from the absorbency at 280 nm simultaneously.

(1-C) Bridging of Maleimide-Conjugated Anti-mouse CD3ε Monoclonal Antibodies and Reduced Anti-PD-1 Antibodies Maleimide-conjugated anti-mouse CD3ε monoclonal antibodies and Reduced anti-PD-1 antibodies were mixed at the rate of 1:4 and incubated at 15° C. for 18 hours. Then the reaction mixture was size-fractionated by gel filtration using Sephacryl S-300 [Sodium phosphate (0.1M, pH7.0)] and major peak fractions were collected by monitoring the absorbency at 280 nm. The protein content was calculated from the absorbency at 280 nm simultaneously.

(2) Preparation of Anti-PD-1/Anti-TCR Hybrid Fab Antibodies (2-A) Preparation of F(ab')$_2$ Fraction of Anti-PD-1 Antibodies Antibodies against mouse PD-1 (produced by the hybridoma cells named (J43) and deposited as international deposition Accession number FERM BP-8118) were substituted with pepsin-buffer [(sodium acetate 0.1M, pH4.5), NaCl (0.1M)], added with pepsin (final concentration of 0.2 mg/ml), and digested for 48 hours at 37° C. Then the reaction mixture was size-fractionated by gel filtration using Sephacryl S-200 [Tris-HCl (0.2M, pH8.0), EDTA (10 mM)] and major peak fractions (F(ab')$_2$ fraction) were collected by monitoring the absorbency at 280 nm. The protein content was calculated from the absorbency at 280 nm simultaneously.

(2-B) Preparation of $Fab_{SH}$ Fraction of Anti-PD-1 Antibodies 2-mercaptoethanol (final concentration of 20 mM) was added to reduce the F(ab')$_2$ fraction at 30° C. for 30 minutes. After cooling the reaction mixture on ice, it was size-fractionated by gel filtration using Sephacryl S-200 [sodium acetate (50 mM, pH6.3), EDTA (1 mM)] and major peak fractions ($Fab_{SH}$ fraction) were collected by monitoring the absorbency at 280 nm. The protein content was calculated from the absorbency at 280 nm simultaneously.

(2-C) Preparation of F(ab')$_2$ Fraction of Anti-mouse CD3ε Monoclonal Antibodies Anti-mouse CD3ε monoclonal antibodies (manufactured by Pharmingen) were substituted with pepsin-buffer [(sodium acetate 0.1M, pH4.5), NaCl (0.1M)], added with pepsin (final concentration of 0.2 mg/ml), and digested for 48 hours at 37° C. Then the reaction mixture was size-fractionated by gel filtration using Sephacryl S-200 [Tris-HCl (0.2M, pH8.0), EDTA (10 mM)] and major peak fractions (F(ab')$_2$ fraction) were collected by monitoring the absorbency at 280 nm. The protein content was calculated from the absorbency at 280 nm simultaneously.

(2-D) Preparation of $Fab_{SH}$ Fraction of Anti-mouse CD3ε Monoclonal Antibodies 2-mercaptoethanol (final concentration of 20 mM) was added to reduce the F(ab')$_2$ fraction at 30° C. for 30 minutes. After cooling the reaction mixture on ice, it was size-fractionated by gel filtration using Sephacryl S-200 [sodium acetate (50 mM, pH6.3), EDTA (1 mM)] and major peak fractions ($Fab_{SH}$ fraction) were collected by monitoring the absorbency at 280 nm. The protein content was calculated from the absorbency at 280 nm simultaneously.

(2-E) Bridging of $Fab_{SH}$ Fraction of Anti-PD-1 Antibodies and $Fab_{SH}$ Fraction of Anti-mouse CD3ε Monoclonal Antibodies Phenylenedimaleimide (manufactured by Aldrich) (final concentration of 4 mM) was added to the $Fab_{SH}$ fraction of anti-PD-1 antibodies prepared in step (2-A), and incubated for 30 minutes at room temperature to prepare J43 $Fab_{mal}$ fraction. The J43 $Fab_{mal}$ fraction and the $Fab_{SH}$ fraction of anti-mouse CD3ε monoclonal antibodies were mixed at the rate of 1:1.3 and incubated for 4 hours at room temperature. Next, an appropriate amount of Tris-HCl (1M, pH8.0) were added to make the pH of the reaction mixture 8.0, 2-mercaptoethanol (final concentration of 20 mM) was added and incubated at 30° C. for 30 minutes. Then iodoacetoamide (manufactured by Sigma) was added (final concentration of 25 mM) and incubated for additional 10 minutes at room temperature under light shielding.

Finally, the reaction mixture was size-fractionated by gel filtration using Sephacryl S-200 [sodium acetate (50 mM, pH6.3), EDTA (1 mM)] and major peak fractions (BsAb fraction) were collected by monitoring the absorbency at 280 nm. The protein content was calculated from the absorbency at 280 nm simultaneously.

EXAMPLE 2

Confirmation of Reactivity of Anti-PD-1/Anti-TCR Hybrid Fab Antibodies on Cell Surface Antigen (PD-1 and CD3)

$1 \times 10^6$ cells were recovered from mPD-1/A20IIA1.6 cells as a PD-1 positive and CD3 negative cell, and naive T cells prepared from mouse spleen cells as a PD-1 negative and CD3 positive cell, respectively. The cells were added with 91 μl of FACS buffer (PBS(−) containing 0.5% BSA, EDTA (2 mM)

and 0.01% NaN₃), 5 μl of mouse serum and 4 μl of hybrid antibodies (2 μg) and incubated for 30 minutes on ice. After washing with PBS(−) once, the cells were added with each 2 μl (1 μg) of second antibodies, fill upped to final 100 μl with FACS buffer, and incubated for 30 minutes on ice. Then they were analyzed by using FACScan. The results were shown in FIG. 1 (in the following figures, hybrid Fab antibody simply referred to as "HFAb").

Analysis whether the prepared anti-PD-1/anti-TCR hybrid Fab antibodies actually react with the cell surface antigens by using FACS$_{sort}$ (manufactured by Becton Dickinson) showed the results that the antibodies reacted with both surface antigens.

EXAMPLE 3

Effect of Anti-PD-1/Anti-TCR Hybrid Fab Antibodies on Activated T Cells (A) Preparation of Spleen T Cells Spleen was excised from BALB/c mouse. After red blood cells were hemolyzed, the spleen cells were washed once with PBS (−) and suspended in medium RPMI 1640 (10% FCS, antibiotics) ($1 \times 10^8$ cells/ml). Next, T cells were prepared by using nylon fiber column (manufactured by WAKO) for T cell separation equilibrated with the medium.

(B) Effect of Anti-PD-1/Anti-TCR Hybrid Fab Antibodies on Activated Spleen T Cells Ninety six-well plates were coated with 0.5 μg/ml and 5 μg/ml of anti-CD3 antibodies (clone KT3, manufactured by Immuntech) at 37° C. for 3 hours. T cells ($2 \times 10^5$ cells/well/ 200 μl) were seeded on the plates, anti-PD-1/anti-TCR hybrid antibodies (0.03, 0.1, 0.3, 1, 3 μg/100 ml) were added, and incubated in a $CO_2$ incubator (at 37° C.). After 72 hours, cytokine (IFN-r, IL-2, IL-4 and IL-10) concentrations in the recovered culture supernatants were measured by using assay kit (manufactured by R & D System).

Figure 2:
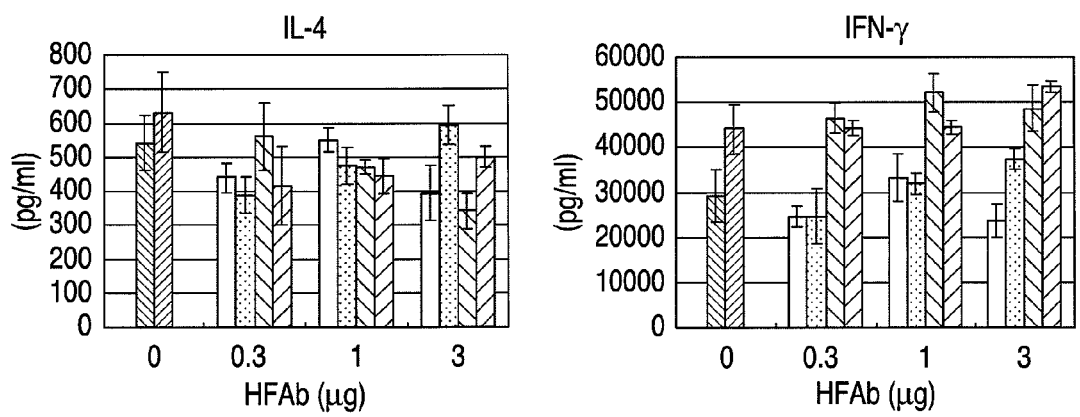
FIG. 2 shows the effect of anti-PD-1/anti-TCR hybrid Fab antibodies on activated T cells.

As the results shown in FIG. 2, after 72 hours when 3 μg of anti-PD-1/anti-TCR hybrid Fab antibodies were used, the results were obtained that the stimulation by the antibodies both in 0.5 μg/ml and 5 μg/ml suppressed the production of IFN-r, IL-4 and IL-10 dominantly.

EXAMPLE 4

Preparation of Anti-PD-1/Anti-BCR Hybrid Fab Antibodies (A) Preparation of F(ab')₂ Fraction of Anti-PD-1 Antibodies Antibodies against mouse PD-1 (the same antibodies as used in Example 1) were substituted with pepsin-buffer [(sodium acetate 0.1M, pH4.5), NaCl (0.1M)], added with pepsin (manufactured by SIGMA) (final concentration of 0.2 mg/ml), and digested at 37° C. for 48 hours. Then the reaction mixture was size-fractionated by gel filtration using Sephacryl S-200 (manufactured by AmarshamParmacia) [Tris-HCl (0.2M, pH8.0), EDTA (10 mM)] and major peak fractions (F(ab')₂ fraction) were collected by monitoring the absorbency at 280 nm. The protein content was calculated from the absorbency at 280 nm simultaneously.

(B) Preparation of Fab$_{SH}$ Fraction of Anti-PD-1 Antibodies 2-mercaptoethanol (final concentration of 20 mM) was added to reduce the F(ab')₂ fraction at 30° C. for 30 minutes. After cooling the reaction mixture on ice, it was size-fractionated by gel filtration using Sephacryl S-200 [sodium acetate (50 mM, pH6.3), EDTA (1 mM)] and major peak fractions (Fab$_{SH}$ fraction) were collected by monitoring the absorbency at 280 nm. The protein content was calculated from the absorbency at 280 nm simultaneously.

(C) Preparation of F(ab')₂ Fraction of Anti-IgG (H+L) Polyclonal Antibodies

Rabbit anti-mouse IgG (H+L) polyclonal antibodies (manufactured by Zymed) were substituted with pepsin-buffer [(sodium acetate 0.1M, pH4.5), NaCl (0.1M)], added with pepsin (final concentration of 0.2 mg/ml), and digested at 37° C. for 48 hours. Then the reaction mixture was size-fractionated by gel filtration using Sephacryl S-200 [Tris-HCl (0.2M, pH8.0), EDTA (10 mM)] and major peak fractions (F(ab')₂ fraction) were collected by monitoring the absorbency at 280 nm. The protein content was calculated from the absorbency at 280 nm simultaneously.

(D) Preparation of Fab$_{SH}$ Fraction of Anti-IgG (H+L) Polyclonal Antibodies 2-mercaptoethanol (final concentration of 20 mM) was added to reduce the F(ab')₂ fraction at 30° C. for 30 minutes. After cooling the reaction mixture on ice, it was size-fractionated by gel filtration using Sephacryl S-200 [sodium acetate (50 mM, pH6.3), EDTA (1 mM)] and major peak fractions (Fab$_{SH}$ fraction) were collected by monitoring the absorbency at 280 nm. The protein content was calculated from the absorbency at 280 nm simultaneously.

(E) Bridging of Fab$_{SH}$ Fraction of Anti-PD-1 Antibodies and Fab$_{SH}$ Fraction of Anti-IgG (H+L) Polyclonal Antibodies Phenylenedimaleimide (manufactured by Aldrich) (final concentration of 4 mM) was added to the Fab$_{SH}$ fraction of J43 anti-PD-1 antibodies, and incubated for 30 minutes at room temperature to prepare J43 Fab$_{mal}$ fraction. The J43 Fab$_{mal}$ fraction and the Fab$_{SH}$ fraction of anti-IgG (H+L) polyclonal antibodies were mixed at the rate of 1:1.3 and incubated for 4 hours at room temperature. Next, an appropriate amount of Tris-HCl (1M, pH8.0) were added to make the pH of the reaction mixture 8.0, 2-mercaptoethanol (final concentration of 20 mM) was added and incubated at 30° C. for 30 minutes. Then iodoacetoamide (manufactured by SIGMA) was added (final concentration of 25 mM) and incubated for additional 10 minutes at room temperature under light shielding. Finally, the reaction mixture was size-fractionated by gel filtration using Sephacryl S-200 [sodium acetate (50 mM, pH6.3), EDTA (1 mM)] and major peak fractions (BsAb fraction) were collected by monitoring the absorbency at 280 nm. The protein content was calculated from the absorbency at 280 nm simultaneously.

EXAMPLE 5

Effect of Anti-PD-1/Anti-BCR Hybrid Fab Antibodies on B Cell Line (A) Generation of A20IIA1.6 (B Cell Line) that was Forced to Express Mouse PD-1

(1) Construction of Expression Plasmid for Mouse PD-1

DNA fragments of mPD1-flag digested with EcoRI were inserted into the EcoRI site of a commercially available expression vector to construct the expression plasmid mPD1-pA.

(2) Transfection

A20IIA1.6 cells ($1 \times 10^7$) in 325 μl of ice-cold RPMI1640 medium containing 15% FCS and the PD-1 expression plasmid linearized with ScaI in 10 μl of distilled water were incorporated into a Cuvette for electroporation (Gene Pulser Cuvette 0.4 cm electrode gap, 50, BIO RAD), and pulsed under the condition of 250V/960 µF (Gene Pulser, BIO RAD). After leaving at rest for 10 minutes at room temperature, the cells were suspended in 30 ml of medium (RPMI1640 containing 10% FBS, 50 µl of 2-mercaptoethanol, penicillin and streptomycin), diluted thirty fold further, and dispensed onto 96-well plates (103/100 µl/well). After 48 hours, the selection was initiated using final 3 µM of Puromycin to establish the cell line expressing mouse PD-1.

(B) Effect of Anti-PD-1/Anti-BCR Hybrid Fab Antibodies on A20IIA1.6 Cells that was Forced to Express Mouse PD-1

Figure 3:
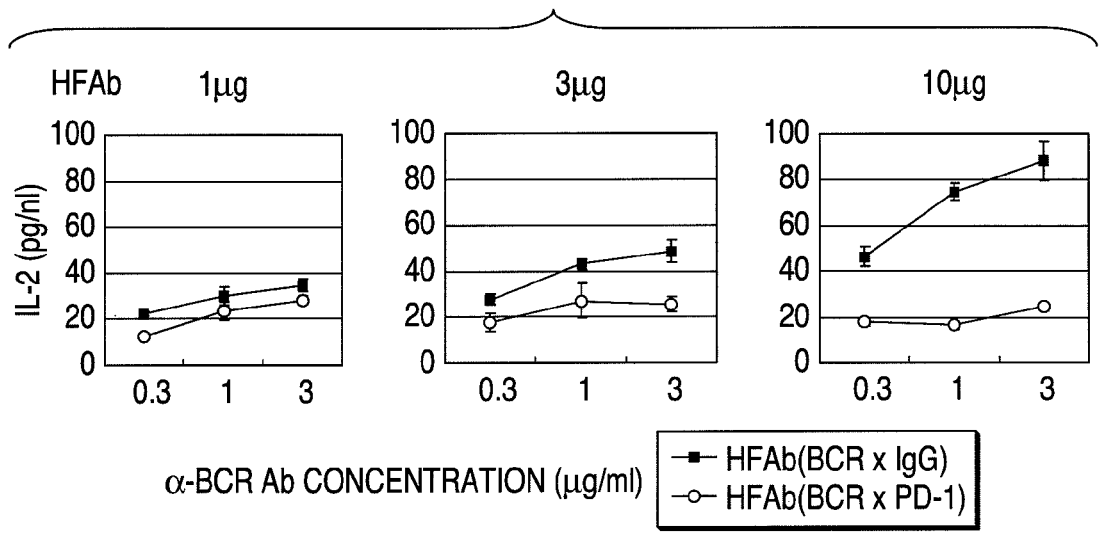
FIG. 3 shows the inhibitory effect of anti-PD-1/anti-BCR hybrid Fab antibodies on the production of IL-2 by anti-BCR antibody stimulation.

A20IIA1.6 cells that was forced to express mouse PD-1 were seeded on 96-well plates ($5 \times 10^5$ cells/100 µl). Anti-PD-1/anti-BCR hybrid Fab antibodies (0, 1, 3, 10 µg/100 µl) were added, 10 minutes later 100 µl of anti-mouse IgG (H+L) F(ab')$_2$ (manufactured by Zymed) (final concentration of 0.3, 1, 3 µg/ml) were dispensed and cultivated for 12 hours in a $CO_2$ incubator (at 37° C.). The culture supernatants were recovered and the concentrations of IL-2 in the culture supernatants were measured by using mouse IL-2 assay kit (manufactured by R & G System). The results were shown in FIG. 3.

The studies using various doses of anti-PD-1/anti-BCR hybrid Fab antibodies and anti-BCR antibodies F(ab')$_2$ showed the suppressive effects of the hybrid Fab antibodies in all cases, regardless of the concentration of anti-BCR antibodies F(ab')$_2$.

(C) Confirmation of SHP-2 Recruitment

Anti-PD-1/anti-BCR hybrid Fab antibodies (0, 1, 3, 10 µg/100 µl) were added to $3 \times 10^6$ of A20IIA1.6 cells (B cell line) that was forced to express mouse PD-1. After 10 minutes, 100 µl of anti-mouse IgG (H+L) F(ab')$_2$ were added and incubated for 5 minutes at room temperature. After discarding the supernatants by centrifugation, the cells were suspended in 200 µl of lysis buffer (composition: Tris-HCl (20 mM, pH7.4), NaCl (150 mM), Na$_2$EDTA (1 mM), EGTA (1 mM), 1% Triton-X100, sodium pyrophosphate (2.5 mM), 1-sodium glycerophosphate (1 mM), Na$_3$VO$_4$ (1 mM), leupeptin (1 µg/ml) and PMSF (1 mM) and left at rest on ice. After 30 minutes, the supernatants were recovered by centrifugation, 20 µl of protein G-cepharose beads (manufactured by Amersham Bioscience) added, and incubated at 4° C. for 30 minutes. After recovering the supernatants by centrifugation, 20 µl of protein G-cepharose beads bound beforehand with anti-FLAG antibodies (manufactured by SIGMA) were added and mixed over night at 4° C.

The beads were washed five times with 400 µl of lysis buffer, added with 20 µl of lysis buffer and 20 µl of 2×SDS sample buffer, and boiled at 100° C. for 5 minutes. After discarding the beads by centrifugation, 15 µl of supernatants were subjected to 4-20% SDS-PAGE. After electrophoresis the gels were substituted with blotting buffer and transferred onto PVDF membrane (manufactured by BIO RAD). Then the membrane was blocked with Block Ace (manufactured by Dainippon Pharmaceuticals) for 1 hour at room temperature.

The membrane was incubated with anti-SHP-2 antibody (manufactured by SANTA CRUZ) diluted 1/200 for 1 hour at room temperature, then washed three times with TBS-T for 10 minutes. Next, the membrane was incubated with HRP-conjugated anti-rabbit Ig antibody (manufactured by Amersham Bioscience) diluted 1/2000 for 1 hour at room temperature, then washed three times with TBS-T for 10 minutes. Finally the membrane was emitted light by using ECT plus detection kit (manufactured by Amersham Bioscience) and analyzed using luminoimager LAS1000 plus (manufactured by FUJI Film).

Figure 4:
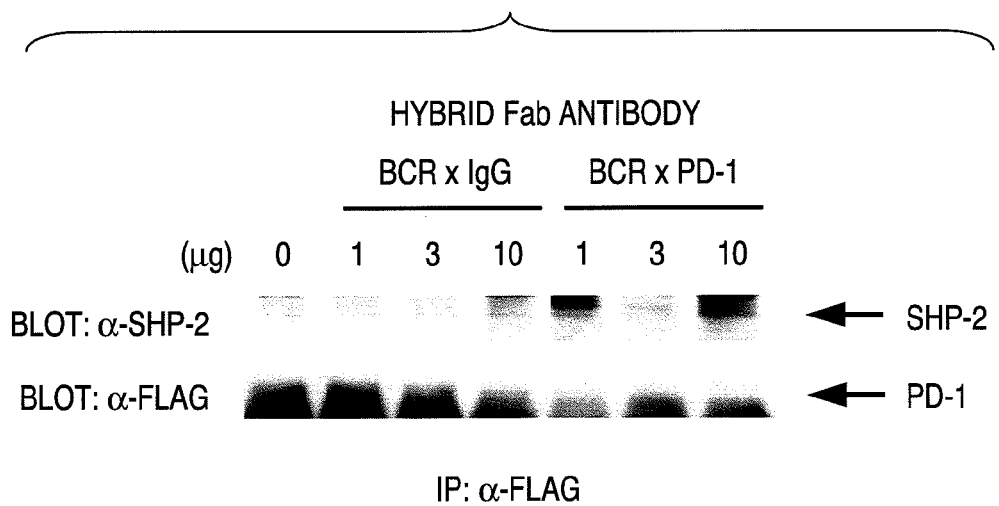
FIG. 4 shows the effect of anti-PD-1/anti-BCR hybrid Fab antibodies on SHP-2 recruitment after anti-BCR antibody stimulation.

Since anti-PD-1/anti-BCR hybrid Fab antibodies suppressed the production of IL-2 from anti-BCR antibody stimulated B cells, the evaluation whether the effects were caused by the recruitment of phosphatase SHP-2 to ITIM of PD-1 was carried out. As shown in FIG. 4, by adjusting the amount of samples with that of PD-1 as a control, the determination of the quantity of SHP-2 recruitment resulted in the obvious recruitment of SHP-2, in 1 and 10 µg, as compared with control hybrid antibodies.

EXAMPLE 6 cDNA Cloning of Anti-Mouse PD-1 Antibody J43

(1) Preparation of Anti-mouse PD-1 Antibody J43

Anti-mouse PD-1 antibody producing hybridoma (J43) cells were cultured in Hybridoma SFM medium (manufactured by Invitrogen) at 37° C. under 5% $CO_2$, a few days after the culture supernatants of hybridoma cells were recovered. IgG fraction was purified from the culture supernatants recovered by using HiTrap Protein G (manufactured by Amersham Bioscience).

(2) Peptide Sequencing

J43 IgG was subjected to 10-20% SDS-PAGE. After electrophoresis the IgG was electrically transferred from the gel onto PVDF membrane (manufactured by BIO RAD). The membrane transferred was stained with coomassie, the membrane fraction containing the light chain of J43 IgG was removed, and amino terminal 15 residues of the light chain were determined by using peptide sequencer Procise492 (manufactured by Applied Biosystems) (SEQ ID NO:1).

(3) Extraction of RNA $5 \times 10^6$ hybridoma cells were lysed with 1 ml of TRIzol (manufactured by Invitrogen). Total RNA was prepared according to the direction of attached document. mRNA was purified from total RNA thus prepared by using Oligotex-MAG mRNA Purification Kit (manufactured by Takara Shuzo).

(4) Cloning of Light Chain cDNA (3'RACE)

Degenerated primer (primer No. 1) was designed based on the amino terminal sequence (YELTQPPSASVNVGE) of the light chain determined by peptide sequencing. 3'RACE was carried out by using 3'-Full RACE Core Set (manufactured by Takara Shuzo) under the following conditions.

Primer No. 1
(SEQ ID NO: 2)
5'-ta(c/t) ga(a/g) ct(g/a/t/c) ac(g/a/t/c) ca(a/g) cc(g/a/t/c) cc-3'

| 1) Synthesis of first strand cDNA | |
|---|---|
| 10 × RNA polymerase chain reaction (PCR) buffer | 2 |
| J43 mRNA (50 ng/µl) | 2 |
| Magnesium chloride (25 mM) | 4 |
| dNTP mixture (each 10 mM) | 2 |
| AMV Reverse Transcriptase XL (5 U/µl) | 1 |
| Oligo dT-3sites Adapter primer (2.5 pmol/µl) | 1 |

-continued

| 1) Synthesis of first strand cDNA | |
|---|---|
| Ribonuclease (RNase) inhibitor (40 U/μl) | 0.5 |
| dH₂O | 7.5 |
| | 15 μl |

30° C. 10 min. → 50° C. 30 min. → 95° C. 5 min. → 4° C. 5 min.

| 2) Polymerase chain reaction (PCR) | |
|---|---|
| First strand cDNA | 1 |
| Primer No. 1 (20 pmol/μl) | 1 |
| Anchorprimer | 1 |
| dH₂O | 22 |
| One shot LA PCR Mix ™ | 25 |
| | 50 μl |

95° C. 5 min. → (94° C. 29 sec., 50° C. 20 sec., 72° C. 60 sec.) × 30 cycles

The PCR products were subjected to electrophoresis using 1% Agarose gel, then the gel was stained by EtBr. DNA fragment was recovered from the gel by using MinElute Gel Extraction Kit (manufactured by Quiagen), the DNA fragment recovered was ligated to pGEM-T Easy Vector (manufactured by Promega) by using DNA Ligation Kit ver.2 (manufactured by Takara Shuzo). *E. coli* DH5α was transformed with the ligated plasmid. Finally, the plasmid was purified from *E. coli* and J43 IgG light chain cDNA was sequenced (SEQ ID NO:3). The deduced amino acid sequence of the cDNA is shown in sequence listing (SEQ ID NO:4)

(5) Cloning of Heavy Chain cDNA (5'RACE)

To perform 5'RACE, primers for constant region were designed based upon the reported information of hamster IgG heavy chain cDNA sequence (GenBank Accession No. U17166). 5'RACE was carried out by using 5'-Full RACE Core Set (manufactured by Takara Shuzo) under the following conditions.

```
Primer No. 2
5'-ccc aag agg tca gga gtt gga-3'     (SEQ ID NO: 5)
(5' phosphorylated)

Primer No. 3
5'-ttg acc agg cat ccc agg gtc-3'     (SEQ ID NO: 6)

Primer No. 4
5'-cgt aag ctg gaa ctc tgg agc-3'     (SEQ ID NO: 7)

Primer No. 5
5'-tgg ttg tgc tgt cac agg cag-3'     (SEQ ID NO: 8)

Primer No. 6
5'-tgc aca cct tcc cat ctg tcc t-3'    (SEQ ID NO: 9)
```

| 1) Synthesis of first strand cDNA | |
|---|---|
| J43 total RNA (2 μg/μl) | 2 |
| 10 × RNA polymerase chain reaction (PCR) buffer | 1.5 |
| Ribonuclease (RNase) inhibitor (40 U/μl) | 0.5 |
| AMV Reverse Transcriptase XL (5 U/μl) | 1 |

-continued

| 1) Synthesis of first strand cDNA | |
|---|---|
| Primer No. 2 (100 pmol/μl) | 2 |
| dH₂O | 8 |
| | 15 μl |

30° C. 10 min. → 50° C. 40 min. → 30° C. 2 min.

| 2) Degeneration of hybrid RNA | |
|---|---|
| First strand cDNA | 15 |
| 5 × Hybrid RNA Degeneration buffer | 15 |
| dH₂O | 45 |
| Ribonuclease H (RNaseH) | 1 |
| | 76 μl |

30° C. 1 hour

After the reaction, ethanol precipitation was carried out.

| 3) Cyclization of single chain cDNA by ligation | |
|---|---|
| 5 × RNA (ssDNA) Ligation buffer | 8 |
| 40% Polyethylene glycol (PEG) #6000 | 20 |
| dH₂O | 12 |
| Pellet after ethanol precipitation | 1 |
| T4 RNA ligase | |
| | 41 μl |

15° C. 15 hours

| 4) First PCR | |
|---|---|
| Sample after ligation | 1 |
| Primer No. 3 (5 pmol/μl) | 2 |
| Primer No. 4 (5 pmol/μl) | 2 |
| dH₂O | 20 |
| One shot LA PCR Mix ™ | 25 |
| | 50 μl |

94° C. 3 min. → (94° C. 30 sec., 52° C. 30 sec., 72° C. 120 sec.) × 25 cycles

| 5) Second PCR | |
|---|---|
| Product of first PCR | 2 |
| Primer No. 5 (5 pmol/μl) | 2 |
| Primer No. 6 (5 pmol/μl) | 2 |
| dH₂O | 20 |
| One shot LA PCR Mix ™ | 25 |
| | 50 μl |

94° C. 3 min. → (94° C. 30 sec., 52° C. 30 sec., 72° C. 120 sec.) × 30 cycles

The PCR products were subjected to electrophoresis using 1% Agarose gel, then the gel was stained by EtBr. DNA fragment was recovered from the gel by using MinElute Gel Extraction Kit (manufactured by Quiagen), the DNA fragment recovered was ligated to pGEM-T Easy Vector (manufactured by Promega) by using DNA Ligation Kit ver.2 (manufactured by Takara Shuzo). *E. coli* DH5α was transformed with the ligated plasmid. Finally, the plasmid was purified from *E. coli* and J43 IgG heavy chain cDNA was sequenced (SEQ ID NO:10). The deduced amino acid sequence of the cDNA is shown in sequence listing (SEQ ID NO:11)

EXAMPLE 7 cDNA Cloning of Anti-Mouse CD3ε Antibody (1) Preparation of RNA

Anti-mouse CD3ε antibody producing hybridoma (145-2C11: manufactured by Pharmingen) cells were cultured in Hybridoma SFM medium (manufactured by Invitrogen) at 37° C. under 5% $CO_2$, a few days after 5×10⁶ hybrisoma cells were lysed with 1 ml of TRIzol (manufactured by Invitrogen). Total RNA was prepared according to the direction of attached document.

(1) Preparation of cDNA Library cDNA was synthesized from 2.5 μg of total RNA extracted from hybridoma (145-2C11) cells by oligo-dT prime method using Ready-To-Go You-Prime First-Strand Beads (manufactured by Amersham Pharmacia). Operations and procedures were followed by the instructions of attached document.

(3) cDNA Cloning of Heavy and Light Chains

Based upon the reported cDNA sequence information of heavy chain variable region of hybridoma 145-2C11 (GenBank Accession No. AF000357), primers No. 7 and No. 8 were designed. Also, based upon the cDNA sequence information of light chain variable region of 145-2C11 (GenBank Accession No. AF000356), primers No. 9 and No. 10 were designed. PCR was carried out using these primers and the cDNA library from hybridoma 145-2C11 as a template.

```
Primer No. 7
                                         (SEQ ID NO: 12)
5'-gag gtg cag ctg gtg gag tct-3'

Primer No. 8
                                         (SEQ ID NO: 13)
5'-tga gga gac ggt gac cat ggt t-3'

Primer No. 9
                                         (SEQ ID NO: 14)
5'-gac atc cag atg acc cag tct c-3'

Primer No. 10
                                         (SEQ ID NO: 15)
5'-ttt gat ttc cag ctt ggt gcc ag-3'
```

| cDNA library | 2 |
|---|---|
| Primer No. 7 or No. 9 (5 pmol/μl) | 2 |
| Primer No. 8 or No. 10 (5 pmol/μl) | 2 |
| $dH_2O$ | 20 |
| One shot LA PCR Mix ™ | 25 |
| | 50 μl |

(94° C. 30 sec., 52° C. 30 sec., 72° C. 120 sec.) × 30 cycles

The PCR products were subjected to electrophoresis using 1% Agarose gel, then the gel was stained by EtBr. DNA fragments were recovered from the gel by using MinElute Gel Extraction Kit (manufactured by Quiagen), the DNA fragments recovered was ligated to pGEM-T Easy Vector (manufactured by Promega) by using DNA Ligation Kit ver.2 (manufactured by Takara Shuzo). *E. coli* DH5α were transformed with the ligated plasmids. Finally, the plasmids were purified from *E. coli*, and both DNA were sequenced. It was confirmed that their sequences were identical to those of GenBank Accession No. AF00357 and GenBank Accession No. AF000356, respectively.

EXAMPLE 8

Constraction of Expression Plasmid for J43-2C11 Bispecific Antibody

Figure 5:
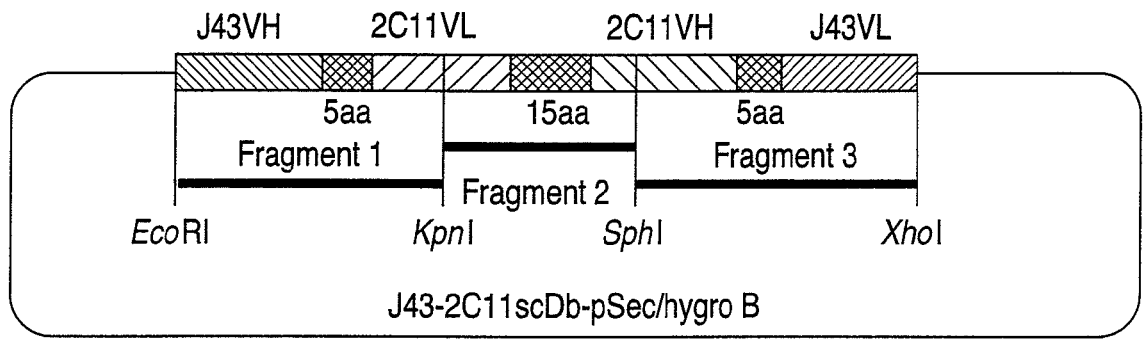
FIG. 5 shows the plasmid J43-2C11scDb-pSec/hygro B for the expression of J43-2C11 bispecific antibody.

J43 IgG heavy chain cDNA and 145-2C11 IgG light chain cDNA were connected by PCR using linker No. 1, No. 2, primer No. 11 and No. 12 to prepare fragment 1 (see FIG. 5). Next, 145-2C11 IgG light chain cDNA and 145-2C11 IgG heavy chain cDNA were connected by PCR using linker No. 3, No. 4, primer No. 13 and No. 14 to prepare fragment 2 (see FIG. 5). 145-2C11 IgG heavy chain cDNA and J43 IgG light chain cDNA were connected by PCR using linker No. 5, No. 6, primer No. 15 and No. 16 to prepare fragment 3 (see FIG. 5).

```
Primer No. 11
                                         (SEQ ID NO: 16)
5'-ttt gaa ttc aga ggt gcg gct tct gga gtc t-3'

Primer No. 12
                                         (SEQ ID NO: 17)
5'-gat cag gag ctt agg agc ttt cc-3'

Primer No. 13
                                         (SEQ ID NO: 18)
5'-cag gcc agt cag gac att agc aa-3'

Primer No. 14
                                         (SEQ ID NO: 19)
5'-taa tgt atg cga ccg act cca gc-3'

Primer No. 15
                                         (SEQ ID NO: 20)
5'-tga ggc ctc tgg att cac ctt ca-3'

Primer No. 16
                                         (SEQ ID NO: 21)
5'-aaa aaa aaa ctc gag gac cta gga cgg tga gct ggg
t-3'

Linker No. 1
                                         (SEQ ID NO: 22)
5'-agg gac cca gtc cac tgt ctc ctc agg tgg agg cgg
ttc aga cat cca gat gac cca gtc tcc at-3'

Linker No. 2
                                         (SEQ ID NO: 23)
5'-tcc ctg gtt ca gtg aca gag gag tcc acc tcc gcc
aag tct gta ggt cta ctg ggt cag agg ta-3'

Linker No. 3
                                         (SEQ ID NO: 24)
5'-acc tgg cac caa gct gga aat caa agg tgg agg cgg
ttc agg cgg agg tgg ctc tgg cgg tgg cgg atc gga
ggt gca gct ggt gga gtc tgg gg-3'

Linker No. 4
                                         (SEQ ID NO: 25)
5'-tgg acc gtg gtt cga cct tta gtt tcc acc tcc gcc
aag tcc gcc tcc acc gag acc gcc acc gcc tag cct
cca cgt cga cca cct cag acc cc-3'

Linker No. 5
                                         (SEQ ID NO: 26)
5'-agg aac cat ggt cac cgt ctc ctc agg tgg agg cgg
ttc ata tga gct gac tca gcc acc ttc ag-3'
```

-continued

Linker No. 6
(SEQ ID NO: 27)
5'-tcc ttg gta cca gtg gca gag gag tcc acc tcc gcc aag tat act cga ctg agt cgg tgg aag tc-3'

| PCR condition for fragments 1, 2 and 3 First PCR | |
|---|---|
| Template 1 | 2 |
| Template 2 | 2 |
| Linker (100 ng/μl) | 2 |
| Linker (100 ng/μl) | 2 |
| $dH_2O$ | 17 |
| One shot LA PCR Mix ™ | 25 |
| | 50 μl |

95° C. 5 min. → (94° C. 30 sec., 40° C. 30 sec., 72° C. 60 sec.) × 20 cycles

| Second PCR | |
|---|---|
| Product of first PCR | 5 |
| Primer (5 pmol/μl) | 2 |
| Primer (5 pmol/μl) | 2 |
| $dH_2O$ | 16 |
| One shot LA PCR Mix ™ | 25 |
| | 50 μl |

95° C. 5 min. → (94° C. 30 sec., 50° C. 30 sec., 72° C. 60 sec.) × 30 cycles

The DNA fragments 1, 2 and 3 and plasmid pBluescriptII SK(+) (manufactured by StrateGene) were digested with restriction enzymes EcoRI/KpnI, KpnI/SphI, SphI/XhoI, EcoRI/XhoI, respectively. After electrophoresis on 1% agarose gel, the DNA fragments were purified from the gel using MinElute Gel Extraction Kit. Next, these three fragments and plasmid pBluescriptII SK(+) (manufactured by StrateGene) were connected using DNA Ligation Kit ver.2 (manufactured by Takara Shuzo), then *E. coli* DH5 (were transformed with the connected plasmid. Plasmid J43-2C11scDb-pBluescriptII SK(+) was prepared from *E. coli*, then the nucleotide sequence of the insert was determined (SEQ ID NO:28). The deduced amino acid sequence is shown in sequence listing (SEQ ID NO:29).

J43-2C11scDb-pBluescriptII SK(+) was digested with restriction enzymes BamHI and XhoI, the BamHI-XhoI fragment out of BamHI-XhoI and BamHI-BamHI fragments generated by the digestion was connected with BamHI/XhoI digested mammalian expression vector pSecTag2/Hygro B (manufactured by Invitrogen). Next, the pSecTag2/Hygro B connected with BamHI-XhoI fragment was digested again with restriction enzyme BamHI, and connected with the other BamHI-BamHI fragment. *E. coli*DH5α were transformed with the connected plasmid. Finally, Plasmid J43-2C11scDb-pSec/Hygro B was prepared from *E. coli*, then the nucleotide sequence of thus prepared J43-2C11 bispecific antibody was determined (SEQ ID NO:30). The deduced amino acid sequence is shown in sequence listing (SEQ ID NO:31).

EXAMPLE 9

Expression of J43-2C11 Bispecific Antibody $6 \times 10^6$ 293 T cells were suspended in 20 ml of medium (DMEM containing 10% FBS) and seeded into 150 mm dish coated with Type Ic collagen. Next day, the cells were washed with 10 ml of DMEM and transfected with J43-2C11scDb-pSec/Hygro B by using LipofectAMINE-plus. After 3 hours, 5 ml of DMEM containing 40% FBS were added to the cells. At day 2, the cells were washed with 10 ml of DMEM, added 20 ml of new DMEM, and the culture supernatant was recovered at day 4.

The cells were discarded by centrifugation, then the supernatant was filtrated using 0.22 μm PVDF filter. The supernatant was enclosed in dialysis tube, dialyzed against PBS containing 40% PEG20000, and concentrated. The concentrated supernatant was purified using HiTrap chelating HP column (manufactured by Amersham Farmacia). To purify further, the antibodies were purified by gel-filtration using Hiprep 16/60 Sephacryl S-200 High Resolution (manufactured by Amersham Farmacia).

EXAMPLE 10

Suppression of T Cell Activation

Spleen was removed from BALB/c mouse, and cells were prepared using CellStrainer (70 μm Nyron). The cells were recovered by centrifugation, and red blood cells were hemolyzed by the addition of hemolysis buffer [$NH_4Cl$ (0.8%), $KCO_3$ (0.1%) and EDTA (1 mM)]. The cells were washed with PBS (−) once, T cells were enriched by using mouse $CD3^+$ T cell enrichment column kit (manufactured by R&D), and suspended in medium (RPMI1640 containing 10% FBS) in the proportion of $5 \times 10^6$ cells/ml. The T cells thus prepared were seeded on 96-well plates ($2 \times 10^5$ cells/100 μl/well), which were coated preliminarily with 5 μg/ml of anti-CD3 antibodies (clone KT3) at 37° C. for 3 hours, added with J43-2C11 bispecific antibody diluted in the medium (0.01, 0.03, 0.1, 0.3, 1 and 3 μg/100 μl), and cultivated for 72 hours at 37° C. under 5% $CO_2$. After 72 hours, the culture supernatants were recovered, and the concentrations of IFN-r in the supernatants were determined by using Quantikine Immunoassay Kit (manufactured by R&D).

Figure 6:
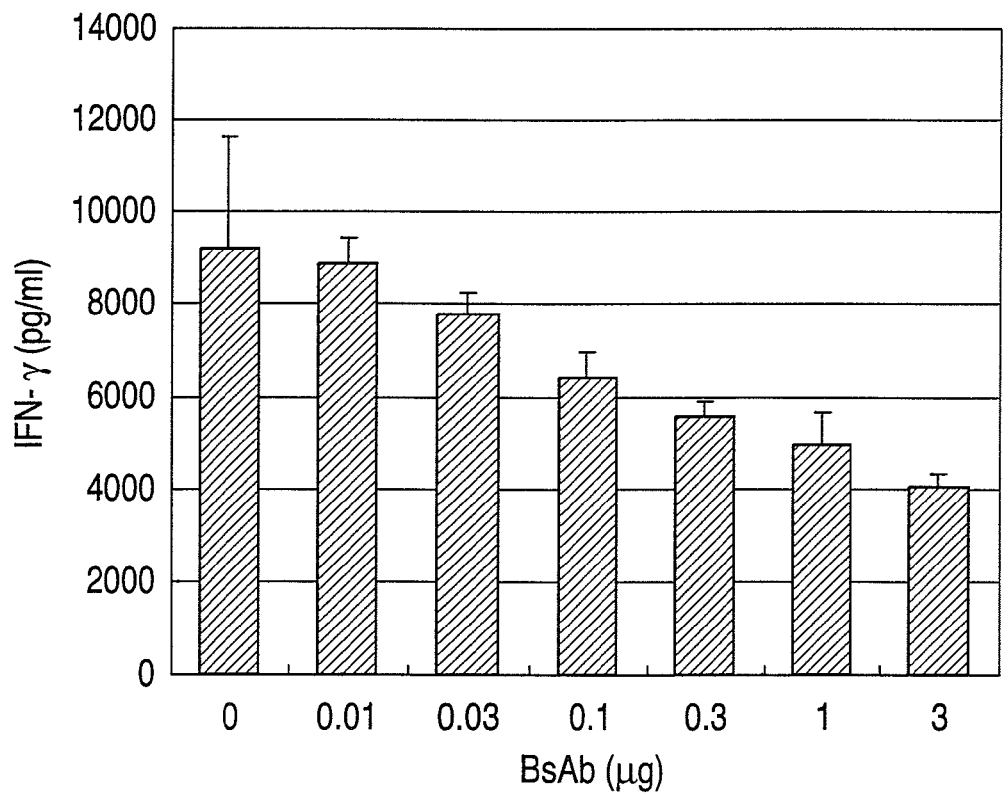
FIG. 6 shows the effect of J43-2C11 bispecific antibodies on the production of IFN-r by activated mouse spleen T cells.

As shown in FIG. 6, J43-2C11 bispecific antibody suppressed dose dependently the production of IFN-r from activated mouse spleen T cells in vitro.

The invention claimed is:

1. An isolated polypeptide consisting of the amino acid sequence of SEQ ID NO: 29.

2. An isolated polypeptide consisting of the amino acid sequence of SEQ ID NO: 31.

* * * * *

SEQUENCE LISTING

<160> NUMBER OF SEQ ID NOS: 31

<210> SEQ ID NO 1
<211> LENGTH: 15
<212> TYPE: PRT
<213> ORGANISM: Mus musculus

<400> SEQUENCE: 1

Tyr Glu Leu Thr Gln Pro Pro Ser Ala Ser Val Asn Val Gly Glu
1               5                   10                  15

<210> SEQ ID NO 2
<211> LENGTH: 20
<212> TYPE: DNA
<213> ORGANISM: Artificial Sequence
<220> FEATURE:
<223> OTHER INFORMATION: Designed DNA based on amino terminal sequence
      of monoclonal antibody J43 light chain to act as a degenerated
      primer
<220> FEATURE:
<221> NAME/KEY: misc_feature
<222> LOCATION: (9)..(9)
<223> OTHER INFORMATION: n = a, c, g or t
<220> FEATURE:
<221> NAME/KEY: misc_feature
<222> LOCATION: (12)..(12)
<223> OTHER INFORMATION: n = a, c, g or t
<220> FEATURE:
<221> NAME/KEY: misc_feature
<222> LOCATION: (18)..(18)
<223> OTHER INFORMATION: n = a, c, g or t

<400> SEQUENCE: 2
taygarctna cncarccncc                                              20

<210> SEQ ID NO 3
<211> LENGTH: 798
<212> TYPE: DNA
<213> ORGANISM: Mus musculus
<220> FEATURE:
<221> NAME/KEY: CDS
<222> LOCATION: (1)..(642)
<220> FEATURE:
<221> NAME/KEY: mat_peptide
<222> LOCATION: (1)..(642)

<400> SEQUENCE: 3

```
tat gag ctg act cag cca cct tca gca tca gtc aat gta gga gag act     48
Tyr Glu Leu Thr Gln Pro Pro Ser Ala Ser Val Asn Val Gly Glu Thr
1               5                   10                  15 gtc aaa atc acc tgc tct ggg gac caa ttg ccg aaa tat ttt gca gat     96
Val Lys Ile Thr Cys Ser Gly Asp Gln Leu Pro Lys Tyr Phe Ala Asp
            20                  25                  30 tgg ttt cat caa agg tca gac cag acc att ttg caa gtg ata tat gat    144
Trp Phe His Gln Arg Ser Asp Gln Thr Ile Leu Gln Val Ile Tyr Asp
        35                  40                  45 gat aat aag cgc ccc tcg ggg atc cct gaa aga atc tct ggg tcc agc    192
Asp Asn Lys Arg Pro Ser Gly Ile Pro Glu Arg Ile Ser Gly Ser Ser
    50                  55                  60 tca ggg aca aca gcc acc ttg acc atc aga gat gtc cgg gct gag gat    240
Ser Gly Thr Thr Ala Thr Leu Thr Ile Arg Asp Val Arg Ala Glu Asp
65                  70                  75                  80 gaa ggt gac tat tac tgt ttc tca gga tat gtt gat agt gat agc aaa    288
Glu Gly Asp Tyr Tyr Cys Phe Ser Gly Tyr Val Asp Ser Asp Ser Lys
                85                  90                  95 ttg tat gtt ttt ggc agc gga acc cag ctc acc gtc cta ggt gga ccc    336
Leu Tyr Val Phe Gly Ser Gly Thr Gln Leu Thr Val Leu Gly Gly Pro
            100                 105                 110 aag tct tct ccc aaa gtc aca gtg ttt cca cct tca cct gag gag ctc    384
Lys Ser Ser Pro Lys Val Thr Val Phe Pro Pro Ser Pro Glu Glu Leu
        115                 120                 125 cgg aca aac aaa gcc aca ctg gtg tgt ctg gtt aat gac ttc tac ccg    432
Arg Thr Asn Lys Ala Thr Leu Val Cys Leu Val Asn Asp Phe Tyr Pro
```

```
                130                 135                 140
ggt tct gca aca gtg acc tgg aag gca aat gga gca act atc aat gat    480
Gly Ser Ala Thr Val Thr Trp Lys Ala Asn Gly Ala Thr Ile Asn Asp
145                 150                 155                 160 ggg gtg aag act aca aag cct tcc aaa cag ggc caa aac tac atg acc    528
Gly Val Lys Thr Thr Lys Pro Ser Lys Gln Gly Gln Asn Tyr Met Thr
                165                 170                 175 agc agc tac cta agt ttg aca gca gac cag tgg aaa tct cac aac agg    576
Ser Ser Tyr Leu Ser Leu Thr Ala Asp Gln Trp Lys Ser His Asn Arg
            180                 185                 190 gtt tcc tgc caa gtt acc cat gaa ggg gaa act gtg gag aag agt ttg    624
Val Ser Cys Gln Val Thr His Glu Gly Glu Thr Val Glu Lys Ser Leu
        195                 200                 205 tcc cct gca gaa tgt ctc taggagccca gtcttttct tagcccagga            672
Ser Pro Ala Glu Cys Leu
    210 agcctggagc tacgggaccc agaatgtggt cttctctcta ttctatcaat ctcaaacctt   732 ctgctcttac ccactgagta ttcaataaag tatcattagt taatcaaaaa aaaaaaaaaa   792 acaaaa                                                             798

<210> SEQ ID NO 4
<211> LENGTH: 214
<212> TYPE: PRT
<213> ORGANISM: Mus musculus

<400> SEQUENCE: 4

Tyr Glu Leu Thr Gln Pro Pro Ser Ala Ser Val Asn Val Gly Glu Thr
1               5                   10                  15

Val Lys Ile Thr Cys Ser Gly Asp Gln Leu Pro Lys Tyr Phe Ala Asp
            20                  25                  30

Trp Phe His Gln Arg Ser Asp Gln Thr Ile Leu Gln Val Ile Tyr Asp
        35                  40                  45

Asp Asn Lys Arg Pro Ser Gly Ile Pro Glu Arg Ile Ser Gly Ser Ser
    50                  55                  60

Ser Gly Thr Thr Ala Thr Leu Thr Ile Arg Asp Val Arg Ala Glu Asp
65                  70                  75                  80

Glu Gly Asp Tyr Tyr Cys Phe Ser Gly Tyr Val Asp Ser Asp Ser Lys
                85                  90                  95

Leu Tyr Val Phe Gly Ser Gly Thr Gln Leu Thr Val Leu Gly Gly Pro
            100                 105                 110

Lys Ser Ser Pro Lys Val Thr Val Phe Pro Pro Ser Pro Glu Glu Leu
        115                 120                 125

Arg Thr Asn Lys Ala Thr Leu Val Cys Leu Val Asn Asp Phe Tyr Pro
    130                 135                 140

Gly Ser Ala Thr Val Thr Trp Lys Ala Asn Gly Ala Thr Ile Asn Asp
145                 150                 155                 160

Gly Val Lys Thr Thr Lys Pro Ser Lys Gln Gly Gln Asn Tyr Met Thr
                165                 170                 175

Ser Ser Tyr Leu Ser Leu Thr Ala Asp Gln Trp Lys Ser His Asn Arg
            180                 185                 190

Val Ser Cys Gln Val Thr His Glu Gly Glu Thr Val Glu Lys Ser Leu
        195                 200                 205

Ser Pro Ala Glu Cys Leu
    210
```

```
<210> SEQ ID NO 5
<211> LENGTH: 21
<212> TYPE: DNA
<213> ORGANISM: Cricetulus migratorius
<220> FEATURE:
<221> NAME/KEY: modified_base
<222> LOCATION: (1)..(1)
<223> OTHER INFORMATION: phosphorylated

<400> SEQUENCE: 5
cccaagaggt caggagttgg a                                              21

<210> SEQ ID NO 6
<211> LENGTH: 21
<212> TYPE: DNA
<213> ORGANISM: Cricetulus migratorius

<400> SEQUENCE: 6
ttgaccaggc atcccagggt c                                              21

<210> SEQ ID NO 7
<211> LENGTH: 21
<212> TYPE: DNA
<213> ORGANISM: Cricetulus migratorius

<400> SEQUENCE: 7
cgtaagctgg aactctggag c                                              21

<210> SEQ ID NO 8
<211> LENGTH: 21
<212> TYPE: DNA
<213> ORGANISM: Cricetulus migratorius

<400> SEQUENCE: 8
tggttgtgct gtcacaggca g                                              21

<210> SEQ ID NO 9
<211> LENGTH: 22
<212> TYPE: DNA
<213> ORGANISM: Cricetulus migratorius

<400> SEQUENCE: 9
tgcacacctt cccatctgtc ct                                             22

<210> SEQ ID NO 10
<211> LENGTH: 548
<212> TYPE: DNA
<213> ORGANISM: Mus musculus
<220> FEATURE:
<221> NAME/KEY: CDS
<222> LOCATION: (66)..(548)
<220> FEATURE:
<221> NAME/KEY: sig_peptide
<222> LOCATION: (66)..(128)
<220> FEATURE:
<221> NAME/KEY: mat_peptide
<222> LOCATION: (129)..(548)

<400> SEQUENCE: 10
ggaggcagag gactctagcc ctgtcttccc attcagtgag cagcactgaa aacaagacca    60 tcaac atg gga ttg gga ctg cag tgg gtt ttc ttt gtt gct ctt tta aaa   110
      Met Gly Leu Gly Leu Gln Trp Val Phe Phe Val Ala Leu Leu Lys
          -20             -15                 -10 ggt gtc cac tgt gag gtg cgg ctt ctg gag tct ggt gga gga tta gtg    158
Gly Val His Cys Glu Val Arg Leu Leu Glu Ser Gly Gly Gly Leu Val
 -5          -1 1               5                  10
```

```
aag cct gag ggg tca ctg aaa ctc tcc tgt gtg gcc tct gga ttc acc     206
Lys Pro Glu Gly Ser Leu Lys Leu Ser Cys Val Ala Ser Gly Phe Thr
             15                  20                  25 ttc agt gac tat ttc atg agc tgg gtc cgc cag gct cca ggg aag ggg     254
Phe Ser Asp Tyr Phe Met Ser Trp Val Arg Gln Ala Pro Gly Lys Gly
             30                  35                  40 ctg gag tgg gtt gct cac ata tac acg aaa agt tat aat tat gca act     302
Leu Glu Trp Val Ala His Ile Tyr Thr Lys Ser Tyr Asn Tyr Ala Thr
             45                  50                  55 tat tac tcg ggt tcg gtg aaa ggc aga ttc acc atc tcc aga gat gat     350
Tyr Tyr Ser Gly Ser Val Lys Gly Arg Phe Thr Ile Ser Arg Asp Asp
         60                  65                  70 tcc cga agc atg gtc tac ctg caa atg aac aac ctg aga act gag gac     398
Ser Arg Ser Met Val Tyr Leu Gln Met Asn Asn Leu Arg Thr Glu Asp
75                  80                  85                  90 acg gcc act tat tac tgt aca aga gat gga agc gga tat ccc tct ctg     446
Thr Ala Thr Tyr Tyr Cys Thr Arg Asp Gly Ser Gly Tyr Pro Ser Leu
                 95                 100                 105 gat ttc tgg ggt caa ggg acc caa gtc act gtc tca gcc aca aca         494
Asp Phe Trp Gly Gln Gly Thr Gln Val Thr Val Ser Ser Ala Thr Thr
                110                 115                 120 aca gcc cca tct gtc tat ccc ttg gcc cct gcc tgt gac agc aca acc     542
Thr Ala Pro Ser Val Tyr Pro Leu Ala Pro Ala Cys Asp Ser Thr Thr
            125                 130                 135 aaa tcg                                                              548
Lys Ser
    140

<210> SEQ ID NO 11
<211> LENGTH: 161
<212> TYPE: PRT
<213> ORGANISM: Mus musculus

<400> SEQUENCE: 11

Met Gly Leu Gly Leu Gln Trp Val Phe Phe Val Ala Leu Leu Lys Gly
    -20                 -15                 -10

Val His Cys Glu Val Arg Leu Leu Glu Ser Gly Gly Gly Leu Val Lys
-5                  -1   1                5                  10

Pro Glu Gly Ser Leu Lys Leu Ser Cys Val Ala Ser Gly Phe Thr Phe
                15                  20                  25

Ser Asp Tyr Phe Met Ser Trp Val Arg Gln Ala Pro Gly Lys Gly Leu
            30                  35                  40

Glu Trp Val Ala His Ile Tyr Thr Lys Ser Tyr Asn Tyr Ala Thr Tyr
        45                  50                  55

Tyr Ser Gly Ser Val Lys Gly Arg Phe Thr Ile Ser Arg Asp Asp Ser
60                  65                  70                  75

Arg Ser Met Val Tyr Leu Gln Met Asn Asn Leu Arg Thr Glu Asp Thr
                80                  85                  90

Ala Thr Tyr Tyr Cys Thr Arg Asp Gly Ser Gly Tyr Pro Ser Leu Asp
            95                 100                 105

Phe Trp Gly Gln Gly Thr Gln Val Thr Val Ser Ser Ala Thr Thr Thr
        110                 115                 120

Ala Pro Ser Val Tyr Pro Leu Ala Pro Ala Cys Asp Ser Thr Thr Lys
    125                 130                 135

Ser
140
```

```
<210> SEQ ID NO 12
<211> LENGTH: 21
<212> TYPE: DNA
<213> ORGANISM: Mus musculus

<400> SEQUENCE: 12
gaggtgcagc tggtggagtc t                                          21

<210> SEQ ID NO 13
<211> LENGTH: 22
<212> TYPE: DNA
<213> ORGANISM: Mus musculus

<400> SEQUENCE: 13
tgaggagacg gtgaccatgg tt                                         22

<210> SEQ ID NO 14
<211> LENGTH: 22
<212> TYPE: DNA
<213> ORGANISM: Mus musculus

<400> SEQUENCE: 14
gacatccaga tgacccagtc tc                                         22

<210> SEQ ID NO 15
<211> LENGTH: 23
<212> TYPE: DNA
<213> ORGANISM: Mus musculus

<400> SEQUENCE: 15
tttgatttcc agcttggtgc cag                                        23

<210> SEQ ID NO 16
<211> LENGTH: 31
<212> TYPE: DNA
<213> ORGANISM: Mus musculus

<400> SEQUENCE: 16
tttgaattca gaggtgcggc ttctggagtc t                               31

<210> SEQ ID NO 17
<211> LENGTH: 23
<212> TYPE: DNA
<213> ORGANISM: Mus musculus

<400> SEQUENCE: 17
gatcaggagc ttaggagctt tcc                                        23

<210> SEQ ID NO 18
<211> LENGTH: 23
<212> TYPE: DNA
<213> ORGANISM: Mus musculus

<400> SEQUENCE: 18
caggccagtc aggacattag caa                                        23

<210> SEQ ID NO 19
<211> LENGTH: 23
<212> TYPE: DNA
<213> ORGANISM: Mus musculus

<400> SEQUENCE: 19
taatgtatgc gaccgactcc agc                                        23
```

```
<210> SEQ ID NO 20
<211> LENGTH: 23
<212> TYPE: DNA
<213> ORGANISM: Mus musculus

<400> SEQUENCE: 20
tgaggcctct ggattcacct tca                                              23

<210> SEQ ID NO 21
<211> LENGTH: 37
<212> TYPE: DNA
<213> ORGANISM: Mus musculus

<400> SEQUENCE: 21
aaaaaaaaac tcgaggacct aggacggtga gctgggt                               37

<210> SEQ ID NO 22
<211> LENGTH: 65
<212> TYPE: DNA
<213> ORGANISM: Artificial Sequence
<220> FEATURE:
<223> OTHER INFORMATION: Designed DNA to act as a linker between the
      heavy chain of J43 and the light chain of 145-2C11

<400> SEQUENCE: 22
agggacccaa gtcactgtct cctcaggtgg aggcggttca gacatccaga tgacccagtc      60
tccat                                                                  65

<210> SEQ ID NO 23
<211> LENGTH: 65
<212> TYPE: DNA
<213> ORGANISM: Artificial Sequence
<220> FEATURE:
<223> OTHER INFORMATION: Designed DNA to act as a linker between the
      heavy chain of J43 and the light chain of 145-2C11

<400> SEQUENCE: 23
tccctgggtt cagtgacaga ggagtccacc tccgccaagt ctgtaggtct actgggtcag      60
aggta                                                                  65

<210> SEQ ID NO 24
<211> LENGTH: 95
<212> TYPE: DNA
<213> ORGANISM: Artificial Sequence
<220> FEATURE:
<223> OTHER INFORMATION: Designed DNA to act as a linker between the
      heavy and light chains of 145-2C11

<400> SEQUENCE: 24
acctggcacc aagctggaaa tcaaaggtgg aggcggttca ggcggaggtg gctctggcgg      60
tggcggatcg gaggtgcagc tggtggagtc tgggg                                 95

<210> SEQ ID NO 25
<211> LENGTH: 95
<212> TYPE: DNA
<213> ORGANISM: Artificial Sequence
<220> FEATURE:
<223> OTHER INFORMATION: Designed DNA to act as a linker between the
      heavy and light chains of 145-2C11

<400> SEQUENCE: 25
tggaccgtgg ttcgaccttt agtttccacc tccgccaagt ccgcctccac cgagaccgcc      60
accgcctagc ctccacgtcg accacctcag acccc                                 95
```

-continued

<210> SEQ ID NO 26
<211> LENGTH: 65
<212> TYPE: DNA
<213> ORGANISM: Artificial Sequence
<220> FEATURE:
<223> OTHER INFORMATION: Designed DNA to act as a linker between the
      heavy chain of 145-2C11 and the light chain of J43

<400> SEQUENCE: 26
aggaaccatg gtcaccgtct cctcaggtgg aggcggttca tatgagctga ctcagccacc      60
ttcag                                                                  65

<210> SEQ ID NO 27
<211> LENGTH: 65
<212> TYPE: DNA
<213> ORGANISM: Artificial Sequence
<220> FEATURE:
<223> OTHER INFORMATION: Designed DNA to act as a linker between the
      heavy chain of 145-2C11 and the light chain of J43

<400> SEQUENCE: 27
tccttggtac cagtggcaga ggagtccacc tccgccaagt atactcgact gagtcggtgg      60
aagtc                                                                  65

<210> SEQ ID NO 28
<211> LENGTH: 1437
<212> TYPE: DNA
<213> ORGANISM: Artificial Sequence
<220> FEATURE:
<223> OTHER INFORMATION: Designed DNA to produce the bispecific antibody
<220> FEATURE:
<221> NAME/KEY: CDS
<222> LOCATION: (1)..(1437)

<400> SEQUENCE: 28

```
gag gtg cgg ctt ctg gag tct ggt gga gga tta gtg aag cct gag ggg        48
Glu Val Arg Leu Leu Glu Ser Gly Gly Gly Leu Val Lys Pro Glu Gly
1               5                   10                  15 tca ctg aaa ctc tcc tgt gtg gcc tct gga ttc acc ttc agt gac tat        96
Ser Leu Lys Leu Ser Cys Val Ala Ser Gly Phe Thr Phe Ser Asp Tyr
            20                  25                  30 ttc atg agc tgg gtc cgc cag gct cca ggg aag ggg ctg gag tgg gtt       144
Phe Met Ser Trp Val Arg Gln Ala Pro Gly Lys Gly Leu Glu Trp Val
        35                  40                  45 gct cac ata tac acg aaa agt tat aat tat gca act tat tac tcg ggt       192
Ala His Ile Tyr Thr Lys Ser Tyr Asn Tyr Ala Thr Tyr Tyr Ser Gly
    50                  55                  60 tcg gtg aaa ggc aga ttc acc atc tcc aga gat gat tcc cga agc atg       240
Ser Val Lys Gly Arg Phe Thr Ile Ser Arg Asp Asp Ser Arg Ser Met
65                  70                  75                  80 gtc tac ctg caa atg aac aac ctg aga act gag gac acg gcc act tat       288
Val Tyr Leu Gln Met Asn Asn Leu Arg Thr Glu Asp Thr Ala Thr Tyr
                85                  90                  95 tac tgt aca aga gat gga agc gga tat ccc tct ctg gat ttc tgg ggt       336
Tyr Cys Thr Arg Asp Gly Ser Gly Tyr Pro Ser Leu Asp Phe Trp Gly
            100                 105                 110 caa ggg acc caa gtc act gtc tcc tca ggt gga ggc ggt tca gac atc       384
Gln Gly Thr Gln Val Thr Val Ser Ser Gly Gly Gly Gly Ser Asp Ile
        115                 120                 125 cag atg acc cag tct cca tca tca ctg cct gcc tcc ctg gga gac aga       432
Gln Met Thr Gln Ser Pro Ser Ser Leu Pro Ala Ser Leu Gly Asp Arg
    130                 135                 140
```

```
gtc act atc aat tgt cag gcc agt cag gac att agc aat tat tta aac        480
Val Thr Ile Asn Cys Gln Ala Ser Gln Asp Ile Ser Asn Tyr Leu Asn
145                 150                 155                 160 tgg tac cag cag aaa cca ggg aaa gct cct aag ctc ctg atc tat tat        528
Trp Tyr Gln Gln Lys Pro Gly Lys Ala Pro Lys Leu Leu Ile Tyr Tyr
                165                 170                 175 aca aat aaa ttg gca gat gga gtc cca tca agg ttc agt ggc agt ggt        576
Thr Asn Lys Leu Ala Asp Gly Val Pro Ser Arg Phe Ser Gly Ser Gly
            180                 185                 190 tct ggg aga gat tct tct ttc act atc agc agc ctg gaa tcc gaa gat        624
Ser Gly Arg Asp Ser Ser Phe Thr Ile Ser Ser Leu Glu Ser Glu Asp
        195                 200                 205 att gga tct tat tac tgt caa cag tat tat aac tat ccg tgg acg ttc        672
Ile Gly Ser Tyr Tyr Cys Gln Gln Tyr Tyr Asn Tyr Pro Trp Thr Phe
    210                 215                 220 gga cct ggc acc aag ctg gaa atc aaa ggt gga ggc ggt tca ggc gga        720
Gly Pro Gly Thr Lys Leu Glu Ile Lys Gly Gly Gly Gly Ser Gly Gly
225                 230                 235                 240 ggt ggc tct ggc ggt ggc gga tcg gag gtg cag ctg gtg gag tct ggg        768
Gly Gly Ser Gly Gly Gly Gly Ser Glu Val Gln Leu Val Glu Ser Gly
                245                 250                 255 gga ggc ttg gtg cag cct gga aag tcc ctg aaa ctc tcc tgt gag gcc        816
Gly Gly Leu Val Gln Pro Gly Lys Ser Leu Lys Leu Ser Cys Glu Ala
            260                 265                 270 tct gga ttc acc ttc agc ggc tat ggc atg cac tgg gtc cgc cag gct        864
Ser Gly Phe Thr Phe Ser Gly Tyr Gly Met His Trp Val Arg Gln Ala
        275                 280                 285 cca ggg agg ggg ctg gag tcg gtc gca tac att act agt agt agt att        912
Pro Gly Arg Gly Leu Glu Ser Val Ala Tyr Ile Thr Ser Ser Ser Ile
    290                 295                 300 aat atc aaa tat gct gac gct gtg aaa ggc cgg ttc acc gtc tcc aga        960
Asn Ile Lys Tyr Ala Asp Ala Val Lys Gly Arg Phe Thr Val Ser Arg
305                 310                 315                 320 gac aat gcc aag aac tta ctg ttt cta caa atg aac att ctc aag tct       1008
Asp Asn Ala Lys Asn Leu Leu Phe Leu Gln Met Asn Ile Leu Lys Ser
                325                 330                 335 gag gac aca gcc atg tac tac tgt gca aga ttc gac tgg gac aaa aat       1056
Glu Asp Thr Ala Met Tyr Tyr Cys Ala Arg Phe Asp Trp Asp Lys Asn
            340                 345                 350 tac tgg ggc caa gga acc atg gtc acc gtc tcc tca ggt gga ggc ggt       1104
Tyr Trp Gly Gln Gly Thr Met Val Thr Val Ser Ser Gly Gly Gly Gly
        355                 360                 365 tca tat gag ctg act cag cca cct tca gca tca gtc aat gta gga gag       1152
Ser Tyr Glu Leu Thr Gln Pro Pro Ser Ala Ser Val Asn Val Gly Glu
    370                 375                 380 act gtc aaa atc acc tgc tct ggg gac caa ttg ccg aaa tat ttt gca       1200
Thr Val Lys Ile Thr Cys Ser Gly Asp Gln Leu Pro Lys Tyr Phe Ala
385                 390                 395                 400 gat tgg ttt cat caa agg tca gac cag acc att ttg caa gtg ata tat       1248
Asp Trp Phe His Gln Arg Ser Asp Gln Thr Ile Leu Gln Val Ile Tyr
                405                 410                 415 gat gat aat aag cgc ccc tcg ggg atc cct gaa aga atc tct ggg tcc       1296
Asp Asp Asn Lys Arg Pro Ser Gly Ile Pro Glu Arg Ile Ser Gly Ser
            420                 425                 430 agc tca ggg aca aca gcc acc ttg acc atc aga gat gtc cgg gct gag       1344
Ser Ser Gly Thr Thr Ala Thr Leu Thr Ile Arg Asp Val Arg Ala Glu
        435                 440                 445 gat gaa ggt gac tat tac tgt ttc tca gga tat gtt gat agt gat agc       1392
Asp Glu Gly Asp Tyr Tyr Cys Phe Ser Gly Tyr Val Asp Ser Asp Ser
```

```
                450                 455                 460
aaa ttg tat gtt ttt ggc agc gga acc cag ctc acc gtc cta ggt    1437
Lys Leu Tyr Val Phe Gly Ser Gly Thr Gln Leu Thr Val Leu Gly
465                 470                 475
```

<210> SEQ ID NO 29
<211> LENGTH: 479
<212> TYPE: PRT
<213> ORGANISM: Artificial Sequence
<220> FEATURE:
<223> OTHER INFORMATION: Designed DNA to produce the bispecific antibody

<400> SEQUENCE: 29

```
Glu Val Arg Leu Leu Glu Ser Gly Gly Gly Leu Val Lys Pro Glu Gly
1               5                   10                  15

Ser Leu Lys Leu Ser Cys Val Ala Ser Gly Phe Thr Phe Ser Asp Tyr
                20                  25                  30

Phe Met Ser Trp Val Arg Gln Ala Pro Gly Lys Gly Leu Glu Trp Val
            35                  40                  45

Ala His Ile Tyr Thr Lys Ser Tyr Asn Tyr Ala Thr Tyr Tyr Ser Gly
        50                  55                  60

Ser Val Lys Gly Arg Phe Thr Ile Ser Arg Asp Asp Ser Arg Ser Met
65                  70                  75                  80

Val Tyr Leu Gln Met Asn Asn Leu Arg Thr Glu Asp Thr Ala Thr Tyr
                85                  90                  95

Tyr Cys Thr Arg Asp Gly Ser Gly Tyr Pro Ser Leu Asp Phe Trp Gly
            100                 105                 110

Gln Gly Thr Gln Val Thr Val Ser Ser Gly Gly Gly Gly Ser Asp Ile
        115                 120                 125

Gln Met Thr Gln Ser Pro Ser Ser Leu Pro Ala Ser Leu Gly Asp Arg
130                 135                 140

Val Thr Ile Asn Cys Gln Ala Ser Gln Asp Ile Ser Asn Tyr Leu Asn
145                 150                 155                 160

Trp Tyr Gln Gln Lys Pro Gly Lys Ala Pro Lys Leu Leu Ile Tyr Tyr
                165                 170                 175

Thr Asn Lys Leu Ala Asp Gly Val Pro Ser Arg Phe Ser Gly Ser Gly
            180                 185                 190

Ser Gly Arg Asp Ser Ser Phe Thr Ile Ser Ser Leu Glu Ser Glu Asp
        195                 200                 205

Ile Gly Ser Tyr Tyr Cys Gln Gln Tyr Tyr Asn Tyr Pro Trp Thr Phe
210                 215                 220

Gly Pro Gly Thr Lys Leu Glu Ile Lys Gly Gly Gly Gly Ser Gly Gly
225                 230                 235                 240

Gly Gly Ser Gly Gly Gly Gly Ser Glu Val Gln Leu Val Glu Ser Gly
                245                 250                 255

Gly Gly Leu Val Gln Pro Gly Lys Ser Leu Lys Leu Ser Cys Glu Ala
            260                 265                 270

Ser Gly Phe Thr Phe Ser Gly Tyr Gly Met His Trp Val Arg Gln Ala
        275                 280                 285

Pro Gly Arg Gly Leu Glu Ser Val Ala Tyr Ile Thr Ser Ser Ser Ile
290                 295                 300

Asn Ile Lys Tyr Ala Asp Ala Val Lys Gly Arg Phe Thr Val Ser Arg
305                 310                 315                 320

Asp Asn Ala Lys Asn Leu Leu Phe Leu Gln Met Asn Ile Leu Lys Ser
                325                 330                 335
```

```
Glu Asp Thr Ala Met Tyr Tyr Cys Ala Arg Phe Asp Trp Asp Lys Asn
            340                 345                 350

Tyr Trp Gly Gln Gly Thr Met Val Thr Val Ser Ser Gly Gly Gly Gly
        355                 360                 365

Ser Tyr Glu Leu Thr Gln Pro Pro Ser Ala Ser Val Asn Val Gly Glu
    370                 375                 380

Thr Val Lys Ile Thr Cys Ser Gly Asp Gln Leu Pro Lys Tyr Phe Ala
385                 390                 395                 400

Asp Trp Phe His Gln Arg Ser Asp Gln Thr Ile Leu Gln Val Ile Tyr
                405                 410                 415

Asp Asp Asn Lys Arg Pro Ser Gly Ile Pro Glu Arg Ile Ser Gly Ser
                420                 425                 430

Ser Ser Gly Thr Thr Ala Thr Leu Thr Ile Arg Asp Val Arg Ala Glu
            435                 440                 445

Asp Glu Gly Asp Tyr Tyr Cys Phe Ser Gly Tyr Val Asp Ser Asp Ser
        450                 455                 460

Lys Leu Tyr Val Phe Gly Ser Gly Thr Gln Leu Thr Val Leu Gly
465                 470                 475

<210> SEQ ID NO 30
<211> LENGTH: 1656
<212> TYPE: DNA
<213> ORGANISM: Artificial Sequence
<220> FEATURE:
<223> OTHER INFORMATION: Designed protein to act as the bispecific
      antibody
<220> FEATURE:
<221> NAME/KEY: CDS
<222> LOCATION: (1)..(1653)
<220> FEATURE:
<221> NAME/KEY: sig_peptide
<222> LOCATION: (1)..(63)
<220> FEATURE:
<221> NAME/KEY: mat_peptide
<222> LOCATION: (64)..(1653)

<400> SEQUENCE: 30 atg gag aca gac aca ctc ctg cta tgg gta ctg ctg ctc tgg gtt cca        48
Met Glu Thr Asp Thr Leu Leu Leu Trp Val Leu Leu Leu Trp Val Pro
    -20                 -15                 -10 ggt tcc act ggt gac gcg gcc cag ccg gcc agg cgc gcg cgc gtt acg        96
Gly Ser Thr Gly Asp Ala Ala Gln Pro Ala Arg Arg Ala Arg Arg Thr
 -5              -1  1               5                  10 aag ctt ggt acc gag ctc gga tcc ccc ggg ctg cag gaa ttc gag gtg       144
Lys Leu Gly Thr Glu Leu Gly Ser Pro Gly Leu Gln Glu Phe Glu Val
            15                  20                  25 cgg ctt ctg gag tct ggt gga gga tta gtg aag cct gag ggg tca ctg       192
Arg Leu Leu Glu Ser Gly Gly Gly Leu Val Lys Pro Glu Gly Ser Leu
        30                  35                  40 aaa ctc tcc tgt gtg gcc tct gga ttc acc ttc agt gac tat ttc atg       240
Lys Leu Ser Cys Val Ala Ser Gly Phe Thr Phe Ser Asp Tyr Phe Met
    45                  50                  55 agc tgg gtc cgc cag gct cca ggg aag ggg ctg gag tgg gtt gct cac       288
Ser Trp Val Arg Gln Ala Pro Gly Lys Gly Leu Glu Trp Val Ala His
60                  65                  70                  75 ata tac acg aaa agt tat aat tat gca act tat tac tcg ggt tcg gtg       336
Ile Tyr Thr Lys Ser Tyr Asn Tyr Ala Thr Tyr Tyr Ser Gly Ser Val
                80                  85                  90 aaa ggc aga ttc acc atc tcc aga gat gat tcc cga agc atg gtc tac       384
Lys Gly Arg Phe Thr Ile Ser Arg Asp Asp Ser Arg Ser Met Val Tyr
            95                  100                 105
```

-continued

```
ctg caa atg aac aac ctg aga act gag gac acg gcc act tat tac tgt    432
Leu Gln Met Asn Asn Leu Arg Thr Glu Asp Thr Ala Thr Tyr Tyr Cys
        110                 115                 120 aca aga gat gga agc gga tat ccc tct ctg gat ttc tgg ggt caa ggg    480
Thr Arg Asp Gly Ser Gly Tyr Pro Ser Leu Asp Phe Trp Gly Gln Gly
125                 130                 135 acc caa gtc act gtc tcc tca ggt gga ggc ggt tca gac atc cag atg    528
Thr Gln Val Thr Val Ser Ser Gly Gly Gly Gly Ser Asp Ile Gln Met
140                 145                 150                 155 acc cag tct cca tca tca ctg cct gcc tcc ctg gga gac aga gtc act    576
Thr Gln Ser Pro Ser Ser Leu Pro Ala Ser Leu Gly Asp Arg Val Thr
                160                 165                 170 atc aat tgt cag gcc agt cag gac att agc aat tat tta aac tgg tac    624
Ile Asn Cys Gln Ala Ser Gln Asp Ile Ser Asn Tyr Leu Asn Trp Tyr
            175                 180                 185 cag cag aaa cca ggg aaa gct cct aag ctc ctg atc tat tat aca aat    672
Gln Gln Lys Pro Gly Lys Ala Pro Lys Leu Leu Ile Tyr Tyr Thr Asn
        190                 195                 200 aaa ttg gca gat gga gtc cca tca agg ttc agt ggc agt ggt tct ggg    720
Lys Leu Ala Asp Gly Val Pro Ser Arg Phe Ser Gly Ser Gly Ser Gly
    205                 210                 215 aga gat tct tct ttc act atc agc agc ctg gaa tcc gaa gat att gga    768
Arg Asp Ser Ser Phe Thr Ile Ser Ser Leu Glu Ser Glu Asp Ile Gly
220                 225                 230                 235 tct tat tac tgt caa cag tat tat aac tat ccg tgg acg ttc gga cct    816
Ser Tyr Tyr Cys Gln Gln Tyr Tyr Asn Tyr Pro Trp Thr Phe Gly Pro
                240                 245                 250 ggc acc aag ctg gaa atc aaa ggt gga ggc ggt tca ggc gga ggt ggc    864
Gly Thr Lys Leu Glu Ile Lys Gly Gly Gly Gly Ser Gly Gly Gly Gly
            255                 260                 265 tct ggc ggt ggc gga tcg gag gtg cag ctg gtg gag tct ggg gga ggc    912
Ser Gly Gly Gly Gly Ser Glu Val Gln Leu Val Glu Ser Gly Gly Gly
        270                 275                 280 ttg gtg cag cct gga aag tcc ctg aaa ctc tcc tgt gag gcc tct gga    960
Leu Val Gln Pro Gly Lys Ser Leu Lys Leu Ser Cys Glu Ala Ser Gly
    285                 290                 295 ttc acc ttc agc ggc tat ggc atg cac tgg gtc cgc cag gct cca ggg   1008
Phe Thr Phe Ser Gly Tyr Gly Met His Trp Val Arg Gln Ala Pro Gly
300                 305                 310                 315 agg ggg ctg gag tcg gtc gca tac att act agt agt agt att aat atc   1056
Arg Gly Leu Glu Ser Val Ala Tyr Ile Thr Ser Ser Ser Ile Asn Ile
                320                 325                 330 aaa tat gct gac gct gtg aaa ggc cgg ttc acc gtc tcc aga gac aat   1104
Lys Tyr Ala Asp Ala Val Lys Gly Arg Phe Thr Val Ser Arg Asp Asn
            335                 340                 345 gcc aag aac tta ctg ttt cta caa atg aac att ctc aag tct gag gac   1152
Ala Lys Asn Leu Leu Phe Leu Gln Met Asn Ile Leu Lys Ser Glu Asp
        350                 355                 360 aca gcc atg tac tac tgt gca aga ttc gac tgg gac aaa aat tac tgg   1200
Thr Ala Met Tyr Tyr Cys Ala Arg Phe Asp Trp Asp Lys Asn Tyr Trp
    365                 370                 375 ggc caa gga acc atg gtc acc gtc tcc tca ggt gga ggc ggt tca tat   1248
Gly Gln Gly Thr Met Val Thr Val Ser Ser Gly Gly Gly Gly Ser Tyr
380                 385                 390                 395 gag ctg act cag cca cct tca gca tca gtc aat gta gga gag act gtc   1296
Glu Leu Thr Gln Pro Pro Ser Ala Ser Val Asn Val Gly Glu Thr Val
                400                 405                 410 aaa atc acc tgc tct ggg gac caa ttg ccg aaa tat ttt gca gat tgg   1344
Lys Ile Thr Cys Ser Gly Asp Gln Leu Pro Lys Tyr Phe Ala Asp Trp
            415                 420                 425
```

```
ttt cat caa agg tca gac cag acc att ttg caa gtg ata tat gat gat    1392
Phe His Gln Arg Ser Asp Gln Thr Ile Leu Gln Val Ile Tyr Asp Asp
        430                 435                 440 aat aag cgc ccc tcg ggg atc cct gaa aga atc tct ggg tcc agc tca    1440
Asn Lys Arg Pro Ser Gly Ile Pro Glu Arg Ile Ser Gly Ser Ser Ser
    445                 450                 455 ggg aca aca gcc acc ttg acc atc aga gat gtc cgg gct gag gat gaa    1488
Gly Thr Thr Ala Thr Leu Thr Ile Arg Asp Val Arg Ala Glu Asp Glu
460                 465                 470                 475 ggt gac tat tac tgt ttc tca gga tat gtt gat agt gat agc aaa ttg    1536
Gly Asp Tyr Tyr Cys Phe Ser Gly Tyr Val Asp Ser Asp Ser Lys Leu
                480                 485                 490 tat gtt ttt ggc agc gga acc cag ctc acc gtc cta ggt cct cga gga    1584
Tyr Val Phe Gly Ser Gly Thr Gln Leu Thr Val Leu Gly Pro Arg Gly
            495                 500                 505 ggg ccc gaa caa aaa ctc atc tca gaa gag gat ctg aat agc gcc gtc    1632
Gly Pro Glu Gln Lys Leu Ile Ser Glu Glu Asp Leu Asn Ser Ala Val
        510                 515                 520 gac cat cat cat cat cat cat tga                                    1656
Asp His His His His His His
    525                 530

<210> SEQ ID NO 31
<211> LENGTH: 551
<212> TYPE: PRT
<213> ORGANISM: Artificial Sequence
<220> FEATURE:
<223> OTHER INFORMATION: Designed protein to act as the bispecific
      antibody

<400> SEQUENCE: 31

Met Glu Thr Asp Thr Leu Leu Leu Trp Val Leu Leu Leu Trp Val Pro
        -20                 -15                 -10

Gly Ser Thr Gly Asp Ala Ala Gln Pro Ala Arg Arg Ala Arg Arg Thr
 -5              -1   1               5                  10

Lys Leu Gly Thr Glu Leu Gly Ser Pro Gly Leu Gln Glu Phe Glu Val
             15                  20                  25

Arg Leu Leu Glu Ser Gly Gly Gly Leu Val Lys Pro Glu Gly Ser Leu
         30                  35                  40

Lys Leu Ser Cys Val Ala Ser Gly Phe Thr Phe Ser Asp Tyr Phe Met
     45                  50                  55

Ser Trp Val Arg Gln Ala Pro Gly Lys Gly Leu Glu Trp Val Ala His
 60                  65                  70                  75

Ile Tyr Thr Lys Ser Tyr Asn Tyr Ala Thr Tyr Tyr Ser Gly Ser Val
                 80                  85                  90

Lys Gly Arg Phe Thr Ile Ser Arg Asp Asp Ser Arg Ser Met Val Tyr
             95                 100                 105

Leu Gln Met Asn Asn Leu Arg Thr Glu Asp Thr Ala Thr Tyr Tyr Cys
        110                 115                 120

Thr Arg Asp Gly Ser Gly Tyr Pro Ser Leu Asp Phe Trp Gly Gln Gly
    125                 130                 135

Thr Gln Val Thr Val Ser Ser Gly Gly Gly Ser Asp Ile Gln Met
140                 145                 150                 155

Thr Gln Ser Pro Ser Ser Leu Pro Ala Ser Leu Gly Asp Arg Val Thr
                160                 165                 170

Ile Asn Cys Gln Ala Ser Gln Asp Ile Ser Asn Tyr Leu Asn Trp Tyr
            175                 180                 185
```

```
Gln Gln Lys Pro Gly Lys Ala Pro Lys Leu Leu Ile Tyr Tyr Thr Asn
        190             195                 200
Lys Leu Ala Asp Gly Val Pro Ser Arg Phe Ser Gly Ser Gly Ser Gly
        205             210             215
Arg Asp Ser Ser Phe Thr Ile Ser Ser Leu Glu Ser Glu Asp Ile Gly
220             225             230             235
Ser Tyr Tyr Cys Gln Gln Tyr Tyr Asn Tyr Pro Trp Thr Phe Gly Pro
            240             245                 250
Gly Thr Lys Leu Glu Ile Lys Gly Gly Gly Ser Gly Gly Gly Gly
        255             260             265
Ser Gly Gly Gly Gly Ser Glu Val Gln Leu Val Glu Ser Gly Gly Gly
        270             275             280
Leu Val Gln Pro Gly Lys Ser Leu Lys Leu Ser Cys Glu Ala Ser Gly
        285             290             295
Phe Thr Phe Ser Gly Tyr Gly Met His Trp Val Arg Gln Ala Pro Gly
300             305             310             315
Arg Gly Leu Glu Ser Val Ala Tyr Ile Thr Ser Ser Ser Ile Asn Ile
            320             325             330
Lys Tyr Ala Asp Ala Val Lys Gly Arg Phe Thr Val Ser Arg Asp Asn
            335             340             345
Ala Lys Asn Leu Leu Phe Leu Gln Met Asn Ile Leu Lys Ser Glu Asp
            350             355             360
Thr Ala Met Tyr Tyr Cys Ala Arg Phe Asp Trp Asp Lys Asn Tyr Trp
            365             370             375
Gly Gln Gly Thr Met Val Thr Val Ser Ser Gly Gly Gly Gly Ser Tyr
380             385             390             395
Glu Leu Thr Gln Pro Pro Ser Ala Ser Val Asn Val Gly Glu Thr Val
            400             405             410
Lys Ile Thr Cys Ser Gly Asp Gln Leu Pro Lys Tyr Phe Ala Asp Trp
            415             420             425
Phe His Gln Arg Ser Asp Gln Thr Ile Leu Gln Val Ile Tyr Asp Asp
            430             435             440
Asn Lys Arg Pro Ser Gly Ile Pro Glu Arg Ile Ser Gly Ser Ser Ser
            445             450             455
Gly Thr Thr Ala Thr Leu Thr Ile Arg Asp Val Arg Ala Glu Asp Glu
460             465             470             475
Gly Asp Tyr Tyr Cys Phe Ser Gly Tyr Val Asp Ser Asp Ser Lys Leu
            480             485             490
Tyr Val Phe Gly Ser Gly Thr Gln Leu Thr Val Leu Gly Pro Arg Gly
            495             500             505
Gly Pro Glu Gln Lys Leu Ile Ser Glu Glu Asp Leu Asn Ser Ala Val
        510             515             520
Asp His His His His His His
        525             530
```